(12) United States Patent
Vernetti et al.

(10) Patent No.: US 11,376,580 B2
(45) Date of Patent: Jul. 5, 2022

(54) METHODS AND SYSTEMS COMPRISING MODIFIED PIPETTES FOR TRANSFERRING AND PRESERVING BIOMATERIAL

(71) Applicant: UNIVERSITY OF PITTSBURGH—OF THE COMMONWEALTH SYSTEM OF HIGHER EDUCATION, Pittsburgh, PA (US)

(72) Inventors: Lawrence Vernetti, Wexford, PA (US); John A. Holmes, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 175 days.

(21) Appl. No.: 16/760,187

(22) PCT Filed: Oct. 30, 2018

(86) PCT No.: PCT/US2018/058137
§ 371 (c)(1),
(2) Date: Apr. 29, 2020

(87) PCT Pub. No.: WO2019/089536
PCT Pub. Date: May 9, 2019

(65) Prior Publication Data
US 2020/0346203 A1 Nov. 5, 2020

Related U.S. Application Data

(60) Provisional application No. 62/578,747, filed on Oct. 30, 2017.

(51) Int. Cl.
*B01L 3/02* (2006.01)
*C12M 1/26* (2006.01)
*A61B 10/00* (2006.01)

(52) U.S. Cl.
CPC ..... *B01L 3/0275* (2013.01); *B01L 2200/0647* (2013.01); *B01L 2300/0609* (2013.01)

(58) Field of Classification Search
None
See application file for complete search history.

(56) References Cited

U.S. PATENT DOCUMENTS

| 3,077,780 A | 2/1963 | Takatsy |
| 3,252,331 A * | 5/1966 | Lancaster ............... G01F 19/00 73/864.72 |

(Continued)

FOREIGN PATENT DOCUMENTS

JP 2007-296407 A 11/2007

OTHER PUBLICATIONS

International Search Report and Written Opinion dated Jan. 15, 2019, from International Application No. PCT/US2018/058137, 15 pages.

(Continued)

*Primary Examiner* — Matthew D Krcha
*Assistant Examiner* — Brittany I Fisher
(74) *Attorney, Agent, or Firm* — Meunier Carlin & Curfman LLC

(57) ABSTRACT

The disclosed technology relates to pipette tips, systems thereof, and methods of their use. In one embodiment, a pipette (100) includes a tip (101) with a defined opening (102) for a biological and/or chemical sample, and a securing structure (103) extending from the end of the tip (101) and in communication with the opening (102), the securing structure (103) having at least one mechanical securing member (104) that is configured to secure the biological and/or chemical sample at the tip (101).

18 Claims, 14 Drawing Sheets

(56) References Cited

U.S. PATENT DOCUMENTS

| | | | |
|---|---|---|---|
| 3,855,868 A | | 12/1974 | Sudvaniemi |
| 4,874,114 A | * | 10/1989 | Guigan ................ B01L 3/0293 73/864.11 |
| 5,348,883 A | * | 9/1994 | Togawa ................ B01L 3/508 422/939 |
| 7,799,279 B2 | | 9/2010 | Fulton et al. |
| 10,357,767 B1 | * | 7/2019 | Sternick ................ B01L 3/0275 |
| 2003/0132109 A1 | * | 7/2003 | Bullen ............. G01N 33/48728 204/403.01 |
| 2009/0252590 A1 | * | 10/2009 | Kilper ................... G02B 21/32 414/800 |
| 2010/0092955 A1 | | 4/2010 | Harriman |
| 2014/0332475 A1 | | 11/2014 | Rubin et al. |

OTHER PUBLICATIONS

Hong, H. et al. "Aquatic flower-inspired cell culture platform with simplified medium exchange process for facilitating cell-surface interaction studies", Biomed Microdevices (2016) 18:3.

Altmann, B. et al. "Microstructuring of multiwell plates for three-dimensional cell culture applications by ultrasonic embossing". Biomed Microdevices (2012) 14:291-301.

* cited by examiner

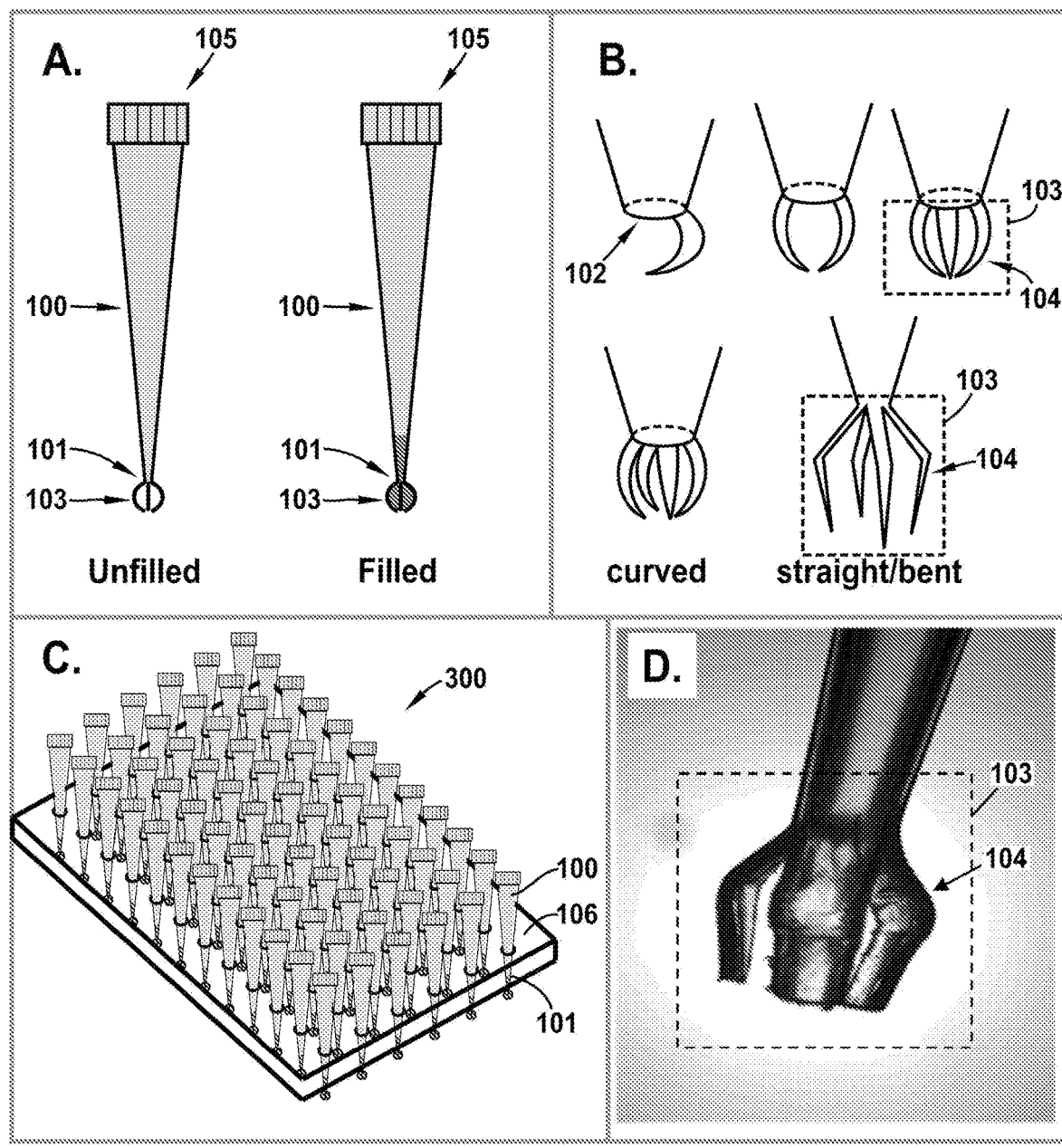
Fig. 1A-D

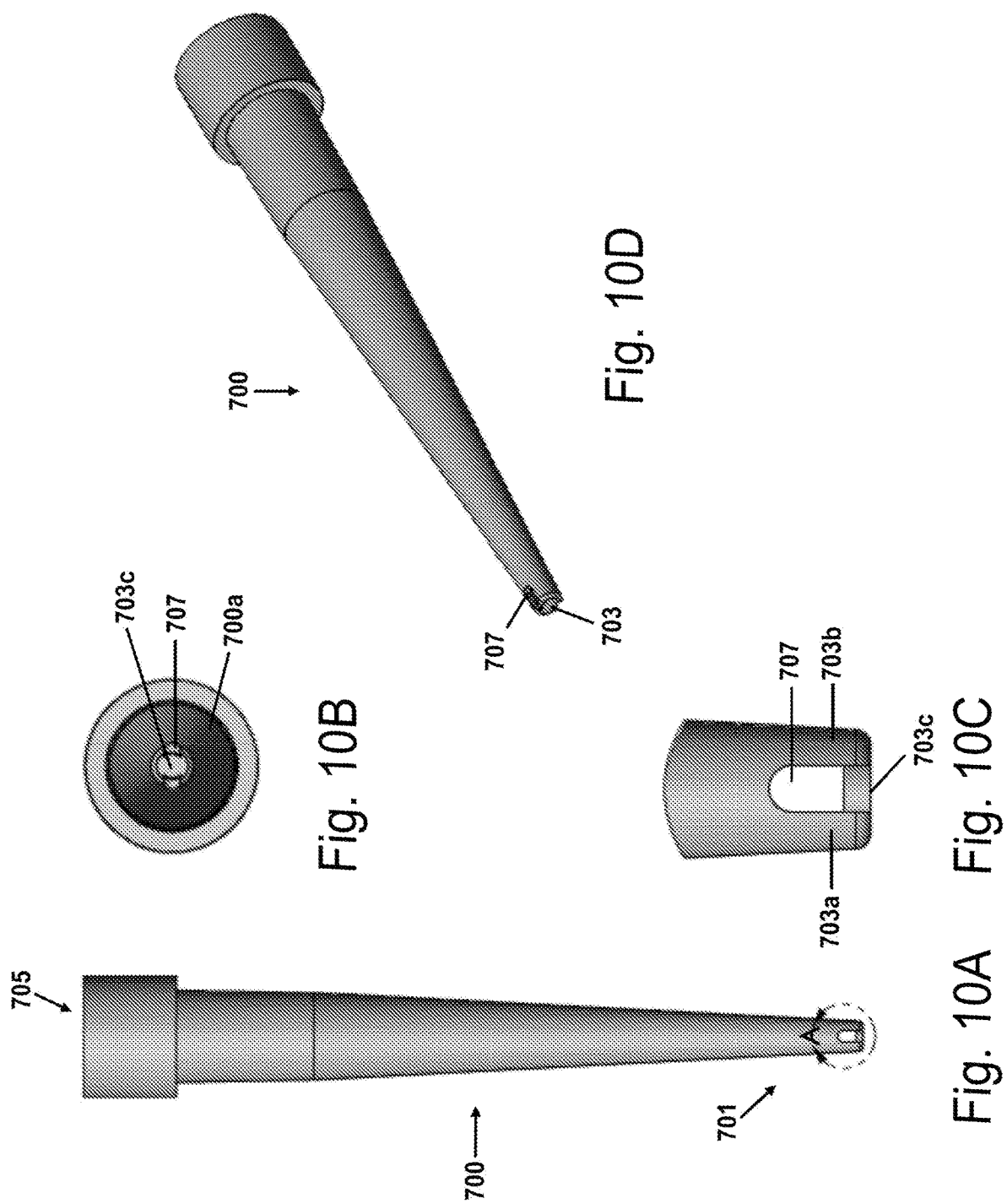

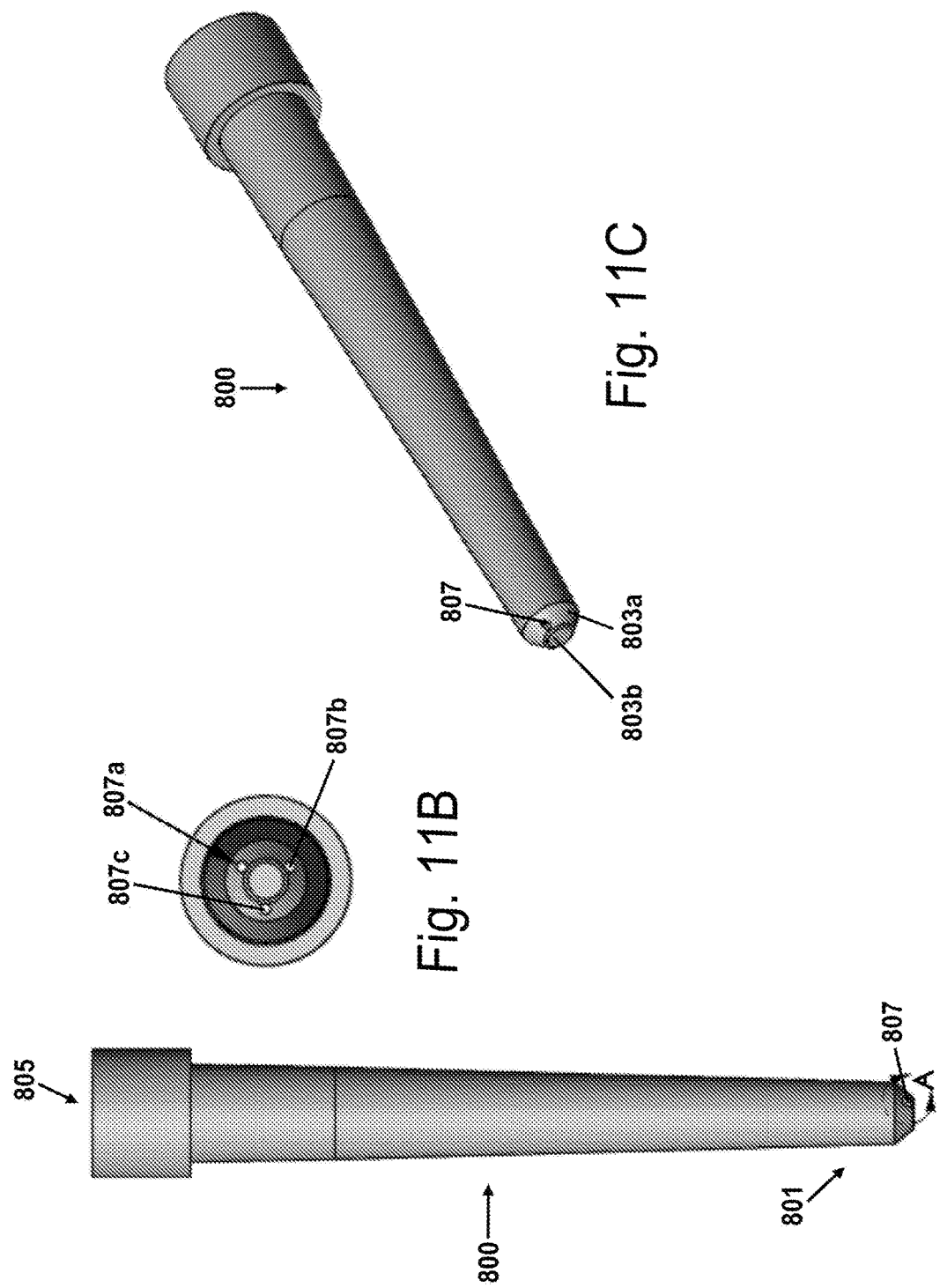

METHODS AND SYSTEMS COMPRISING MODIFIED PIPETTES FOR TRANSFERRING AND PRESERVING BIOMATERIAL

CROSS-REFERENCE TO RELATED APPLICATIONS

This application claims benefit of U.S. Provisional Application No. 62/578,747, filed Oct. 30, 2017, which is incorporated herein by reference in its entirety.

BACKGROUND

The disclosed technology generally relates to modified pipette tips. Pipette tips have been used to manipulate liquid samples for decades. In certain circumstances, it is desirable to provide a pipette tip that may be used with conventional microtiter tubes, standard sized test tubes and microtiter plates. However, pipetting operations conducted with microtiter tubes and test tubes are normally carried out using single channel pipettors while pipetting activities conducted with microtiter plates are typically performed using multichannel pipettors.

Cell-based screens are routinely performed by either quantitative analysis of images acquired by a high-throughput microscope platform or by direct quantification of whole-well signals using a plate reader. Operational ease, simple data output, and over a decade of use in high throughput screens have established the plate reader as a workhorse technology.

Viable intact hepatocytes, isolated from human or laboratory animal livers, offer an experimental model for phase I and phase II drug metabolism studies, as well as enzyme induction studies. Isolated and cultured hepatocytes are also an appropriate model for studying overall liver function. Fresh hepatocytes are obtainable only from liver resections or non-transplantable livers of organ donors. Thus, the availability of viable, fresh liver tissue from humans is inconsistent and overall fairly limited, thus limiting the ability to conduct experiments using such a system, because availability does not always coincide with when such cells are needed. When tissue does become available, the isolated hepatocytes must be cryopreserved and banked for later use.

What is needed in the art are modified pipette tips, methods, and systems thereof, that allow for the precise storage and transportation of cells. It is with respect to these and other considerations that the various embodiments described below are presented.

SUMMARY

In some aspects, the disclosed technology relates to a pipette comprising: a tip with a defined opening for a biological and/or chemical sample; and a securing structure extending from the end of the tip and in communication with the opening, the securing structure having at least one mechanical securing member that is configured to secure the biological and/or chemical sample at the tip. In one embodiment, the at least one mechanical securing member can comprise single, or a plurality, of prong member(s) or claw-type member(s) that are configured to mechanically secure the biological and/or chemical sample. The at least one mechanical securing member can comprise a plurality of prong members and/or claw-type members oriented to substantially surround and hold the biological and/or chemical sample between the members. In another embodiment, the at least one mechanical securing member comprises securing member portions that at least partially define an opening therebetween for receiving the biological and/or chemical sample. The securing structure can comprise defined from one side of the pipette through to an opposite side of the pipette, for receiving the biological and/or chemical sample at the one side of the pipette or the other side of the pipette. The at least one mechanical securing member can comprise a securing member portions that at least partially define an opening therebetween for receiving the biological and/or chemical sample. In one embodiment, the securing member portions can comprise two side portions extending to a solid end tip portion. The opening of the pipette of the securing structure can be substantially rectangular or circular in shape. The securing structure can be configured to protect the secured sample from mechanical stress. The tip and securing structure can be configured to permit the pipette to be insertable and removable into and out of a well of a plate for testing and/or transporting the biological and/or chemical sample. The plate can be a microtiter plate with a plurality of wells. In certain embodiments, the biological and/or chemical sample can be formed as a droplet on the end of the tip and is secured by the securing structure. The biological and/or chemical sample can comprise biological cells, which can be encapsulated within a gel material, such as a gelled agarose cell bead. The pipette can be configured to aspirate a biological and/or chemical sample into the pipette and deliver a biological and/or chemical sample to the tip and into a position to be secured by the securing structure. The securing structure can be configured to adhere the biological and/or chemical sample thereto. At least one mechanical securing member can comprised of a biocompatible material.

In another aspect, disclosed herein is a method, comprising: securing a biological and/or chemical sample by a securing structure of a pipette, the securing structure comprising at least one mechanical securing member that is configured to mechanically secure the sample at the tip of the pipette, wherein the securing structure extends from the end of the tip and is in communication with an opening defined at the tip for receiving and/or delivering a biological and/or chemical sample. Securing the biological and/or chemical sample by the securing structure of the pipette can, in one embodiment, include aspirating or adhering a biological and/or chemical sample into the pipette and delivering a biological and/or chemical sample to the tip and into a position to be secured by the securing structure. In one embodiment, securing the biological and/or chemical sample by the securing structure of the pipette comprises aspirating a biological and/or chemical sample into the pipette and delivering a biological and/or chemical sample to the tip and into a position to be secured by the securing structure. This can comprise adhering the sample thereto. The biological and/or chemical sample can biological cells encapsulated within a gel material. In one embodiment, the method further comprises curing the gel material with the encapsulated cells by exposure to at least one of low temperature, light, ultraviolet (UV) radiation, and pH neutralization. The method can also further comprise inserting the pipette with the secured sample into a well of a plate for testing and/or transporting the sample. In one embodiment, the well can have a biological and/or chemical testing agent for interacting with the secured sample. The secured sample can be retained by the securing structure for at least a part of the testing. At least one mechanical securing member can comprise a single, or a plurality, of prong member(s) or claw-type member(s) that are configured to mechanically secure the biological and/or chemical sample. The securing structure can comprise an opening defined from one side of the pipette through to an opposite side of the pipette, for receiving the biological and/or chemical sample at the one side of the pipette or the other side of the pipette. The at least one mechanical securing member can comprise securing member portions that at least partially define an opening therebetween for receiving the biological and/or chemical sample. The securing member portions can comprise two side portions extending to a solid end tip portion. The opening of the securing structure can be substantially rectangular or circular in shape.

In yet another aspect, disclosed herein is a system for testing and/or transporting a biological and/or chemical sample, comprising: a plate comprising a plurality of wells; a plurality of pipettes, each pipette being configured to be insertable into and removable from a respective well of the plurality of wells, wherein each of the pipettes comprises: a tip with a defined opening for a biological and/or chemical sample, and a securing structure extending from the end of the tip and in communication with the opening, the securing structure having at least one mechanical securing member that is configured to secure the biological and/or chemical sample at the tip. In one embodiment, the at least one mechanical securing member comprises a single, or a plurality of prong member(s) or claw-type member(s) that is configured to mechanically secure the biological and/or chemical sample. The securing structure can comprise an opening defined from one side of the pipette through to an opposite side of the pipette, for receiving the biological and/or chemical sample at the one side of the pipette or the other side of the pipette. At least one mechanical securing member can comprise securing member portions that at least partially define an opening therebetween for receiving the biological and/or chemical sample. The securing member portions can comprise two side portions extending to a solid end tip portion. The opening of the securing structure can be substantially rectangular or circular in shape. At least one of the plurality of wells can comprise a biological and/or chemical testing agent for interacting with the biological and/or chemical sample secured by the securing structure of a respective pipette. At least one of the plurality of wells is configured for receiving a respective pipette for transportation to a means for testing the secured biological and/or chemical sample.

Other aspects and features according to the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIGS. 1A-D show schematic designs for a BioActivator pipette tip in accordance with some embodiments of the present disclosure. FIG. 1A shows a filled (right) and unfilled (left) pipette with a molded claw-like prong tip of a securing structure. FIG. 1B shows various configurations of the molded tip having 1-4 prongs. The prongs can be curved or straight with bends to form claw shape. FIG. 1C shows a final configuration of BioActivator ready to load onto a microtiter plate. FIG. 1D shows a 4-prong pipette tip.

FIG. 1A shows a BioActivator consisting of encapsulated primary human hepatocytes formed into a gelled droplet on the tip of a custom pipette. The BioActivator can be cryopreserved and thawed or used fresh to precondition test compounds for reformatting into 96-, 384- or 1536 microtiter daughter plates, for example. The daughter plates can then be frozen for shipment to an external laboratory for thawing and transfer to the cell or cell-free assay plate. Alternatively, the cryopreserved BioActivator unit can be shipped to the external laboratory for on-site test agent pre-conditioning. FIG. 2B shows the cryopreserved BioActivator, which can be shipped to an external test laboratory where it is thawed and inserted as a co-culture into the media of a cell or cell free assay plate. At the end of the treatment period, the BioActivator can be removed to allow normal test plate processing. The hepatocytes in the BioActivator can be tested for viability at the end of the co-culture incubation period by inserting the pipette tips back into a 384 well plate containing a viability indicator (i.e., CellTiter Gla®). FIG. 2C shows an enlarged schematic showing the BioActivator inserted into an assay plate.

FIG. 8A shows one view of the pipette tip and FIG. 8B shows a side profile view (the view of FIG. 8A rotated 90 degrees). As shown, a defined opening is substantially circular on each side, and as shown in FIG. 8B, securing members with concave-shaped sections (when viewed at the side profile) extend to an end tip portion to partially define the opening.

FIGS. 10A-10D show a pipette with a pipette tip configuration having an opening defined at the tip from one side through to the other, for receiving and/or securing a sample, according to one embodiment of the present disclosure. FIG. 10A shows a front view illustrating the opening and a securing structure. FIG. 10B shows a view taken from an end of the pipette, which illustrates the opening, securing member distal end section, and part of the internal body portion (i.e., walls) of the pipette that run from the proximal end to the distal end. FIG. 10C is an enlarged view of the distal end tip (see dashed and circled area A in FIG. 10A) with the securing structure as shown in FIG. 10A. FIG. 10D is a side perspective view of the pipette shown in FIGS. 10A-10C.

FIGS. 11A-11C show a pipette with a pipette tip configuration having a plurality of openings defined at the tip, according to one embodiment of the present disclosure. FIG. 11A shows a front view illustrating the pipette with one of the openings visible, and FIG. 11B shows a view taken from an end of the pipette, which illustrates the plurality of openings defined in a securing structure. FIG. 11C is a side perspective view of the pipette shown in FIGS. 11A and 11B.

DETAILED DESCRIPTION

Figure 2A:
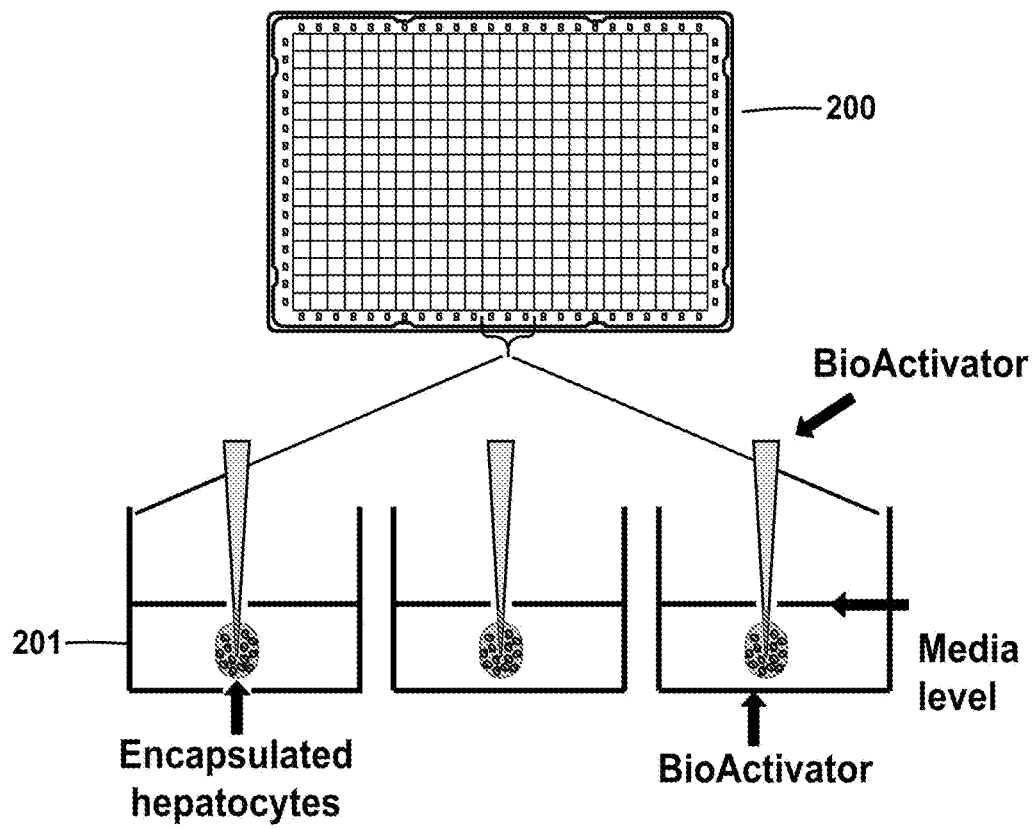
FIGS. 2A-C show a BioActivator (a set of modified pipettes and platform as disclosed herein) in accordance with some example embodiments of the present disclosure.

Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. By "comprising" or "containing" or "including" it is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

In the following description, references are made to the accompanying drawings that form a part hereof and that show, by way of illustration, specific embodiments or examples. In referring to the drawings, like numerals represent like elements throughout the several figures.

As used herein, the terms "molecule" or like terms refer to a biological or biochemical or chemical entity that exists in the form of a chemical molecule or molecules with a definite molecular weight. A molecule or like terms is a chemical, biochemical or biological molecule, regardless of its size. Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecules, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word molecule would include the specific molecule and salts thereof, such as pharmaceutically acceptable salts.

A "test molecule" or like term is a molecule which is used in a method to gain some information about the molecule. A test molecule can be an unknown or a known molecule.

To "modulate," or forms thereof, means increasing, decreasing, or maintaining a cellular activity mediated through a cellular target. It is understood that wherever one of these words is used it is also disclosed that it could be, for example, 1%, 5%, 10%, 20%, 50%, 100%, 500%, or 1000% increased from a control, or it could be, for example, 1%, 5%, 10%, 20%, 50%, or 100% decreased from a control.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems. A cell can include different cell types, such as a cell associated with a specific disease, a type of cell from a specific origin, a type of cell associated with a specific target, or a type of cell associated with a specific physiological function. A cell can also be a native cell, an engineered cell, a transformed cell, an immortalized cell, a primary cell, an embryonic stem cell, an adult stem cell, a cancer stem cell, or a stem cell derived cell. One example of a cell type used with the present methods and systems is a hepatocyte (liver) cell.

"Cell culture" or "cell culturing" refers to the process by which either prokaryotic or eukaryotic cells are grown under controlled conditions. "Cell culture" not only refers to the culturing of cells derived from multicellular eukaryotes, especially animal cells, but also the culturing of complex tissues and organs.

The terms "control" or "control levels" or "control cells" or like terms are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard. For example, a control can refer to the results from an experiment in which the subjects or objects or reagents, etc. are treated as in a parallel experiment except for omission of the procedure or agent or variable, etc. under test and which is used as a standard of comparison in judging experimental effects. Thus, the control can be used to determine the effects related to the procedure or agent or variable etc. In certain circumstances, once a control is performed the control can be used as a standard, in which the control experiment does not have to be performed again and in other circumstances the control experiment should be run in parallel each time a comparison will be made.

Referring now to the Figures, FIGS. 1A-D generally show pipettes (100) in accordance with some embodiments of the present disclosure. Each pipette (100) generally includes, at a distal end portion: a tip (101) with a defined opening (102) for a biological and/or chemical sample; and a securing structure (103) extending from the end portion of the pipette tip (101) and in communication with the opening (102). The securing structure (103) has at least one mechanical securing member (104) that is configured to secure the biological and/or chemical sample at the tip (101). A proximal end of the pipette is referred to herein as a "pipette head" (105), and can be secured to a platform (106). The pipettes (100) and platform (106) together may be referred to herein as the "BioActivator" (300). By "biological and/or chemical sample", for purposes of certain embodiments, is meant any substance that can be secured by the mechanical securing member (104) at the distal end portion tip 101 of the pipette 100). This is discussed in more detail below.

The at least one mechanical securing member (104) can comprise single or multiple prong members or claw-type members that are configured to mechanically secure the biological and/or chemical sample to the pipette end portion tip (101). The various types of securing members (104) in accordance with some embodiments can be seen in FIGS. 1A-1D, for example, and are discussed below. A modified pipette described herein in accordance with various embodiments is designed for a variety of uses, including microtiter tubes, test tubes and microtiter plates, and is compatible with both single channel pipettors or multichannel pipettors.

Now referring to FIGS. 1A-D in more detail, FIGS. 1A-1D show schematic designs for the BioActivator (300) and its associated pipettes (100). FIG. 1A shows a filled and unfilled pipette (100) and a filled and unfilled pipette tip (101). FIG. 1B shows various configurations of a tip (101) having a securing structure (103) with one or more securing members (104). As seen in FIG. 1B, the securing members (104) can surround an opening (102) of the pipette tip. The securing members (104) can be round in shape, such as a semi-circle or other curved feature (see for example "curved" members shown in top row and bottom left of FIG. 1B), or can be straight, or have one or more bends therein (see "straight/bent" configuration) so as to form one or more angles. The angle of the bend in the securing member (104) can vary from 1° to 179°, and the securing member can range from nearly perpendicular to nearly parallel to the opening (102) of the pipette. The members can be configured to protect the secured sample from mechanical stress. There can be one, two, three, four, five, six, seven, eight, or more different securing members (104). When there is more than one securing member (104), they can be spaced uniformly from each other, or can be unevenly spaced. One of skill in the art will appreciate that the securing members (104) can be placed in any configuration about the opening (102). The pipettes (100) themselves, as well as the tips (101) and structure (103) associated therewith, can be any width, length, or depth such that they "fit" into the microtiter plate to which they are paired.

FIG. 1C shows a configuration of the BioActivator (300) ready to load onto a microtiter plate (200) (see, e.g., FIG. 2A). The pipette tip (101) and securing structure (103) are configured to permit the pipette to be insertable and removable into and out of a well (201) of a microtiter plate (200) for testing and/or transporting the biological and/or chemical sample. The tip (101) can be made of any material known in the art to be compatible with cells, such as plastic material such as cyclic polyolefin, syndiotactic polystyrene, polypropylene, atactic polystyrene, PDMS, polyurethane, polycarbonate, or liquid crystal polymer or any other plastic material known to those skilled in the relevant art. The pipettes can be manufactured using injection molding or 3D printers, and can be made of silicone, or any other material useful with 3D printers. The pipette tip can also be coated with any material useful for preserving or enhancing the encapsulated sample. Examples include biological materials, such as proteins, collagen, or other material, or synthetic material used for promoting cell adherence. The surface can also be modified using an oxygen plasma discharge to make the surface more hydrophilic so that it becomes easier for cells to adhere to the surface.

FIG. 1D shows an example of a securing structure (103) with 4 different securing members (104). The pipette can be configured to aspirate a biological and/or chemical sample into the pipette and deliver a biological and/or chemical sample to the tip (101) and into a position to be secured by the securing structure (104). For example, the biological and/or chemical sample can be drawn into the pipette, then pipetted down such that there is a precise, desired amount of the sample at the tip. The sample may adhere to the tip in a desired amount and position, for example as dictated by the design of the securing members in accordance with various embodiments of the present disclosure.

Figure 2B:
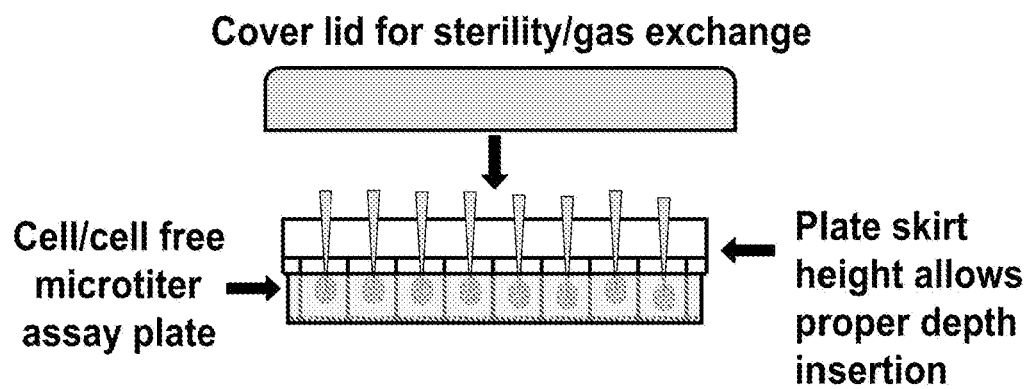
Figure 2C:
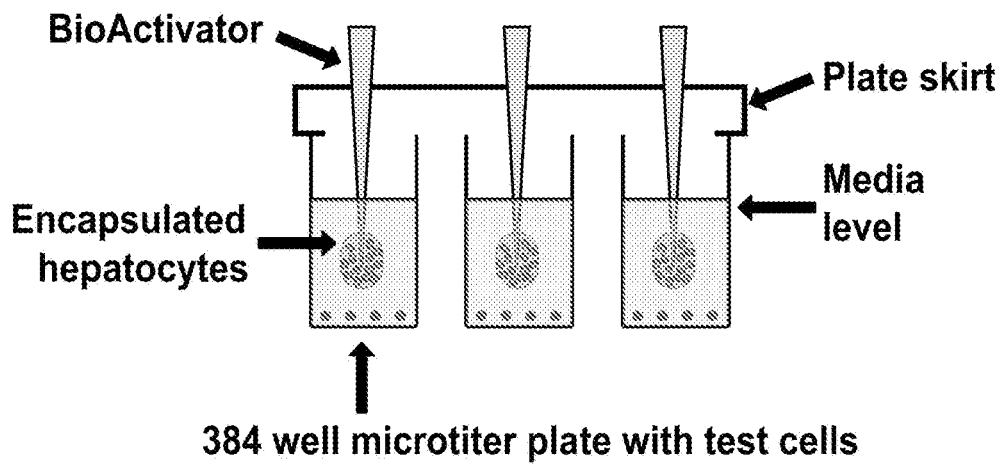

FIG. 2A shows a set of modified pipettes (referred to as a BioActivator) (300). As discussed above, a modified pipette (100) in accordance with various embodiments of the present disclosure can include a tip (101), and on the tip resides at least one mechanical securing structure (103) comprising a plurality of securing members (104), which are prong and/or claw-like, and oriented to substantially surround and hold the biological and/or chemical sample between the members. The BioActivator, when loaded with chemical or biological sample, can be cryopreserved and thawed or used fresh to precondition test compounds. FIGS. 2B and 2C show the cryopreserved BioActivator, which can be used in a variety of methods. For example, the BioActivator can be shipped to an external test laboratory where it can be thawed and inserted as a co-culture into the media of a cell or cell free assay plate.

Figure 3:
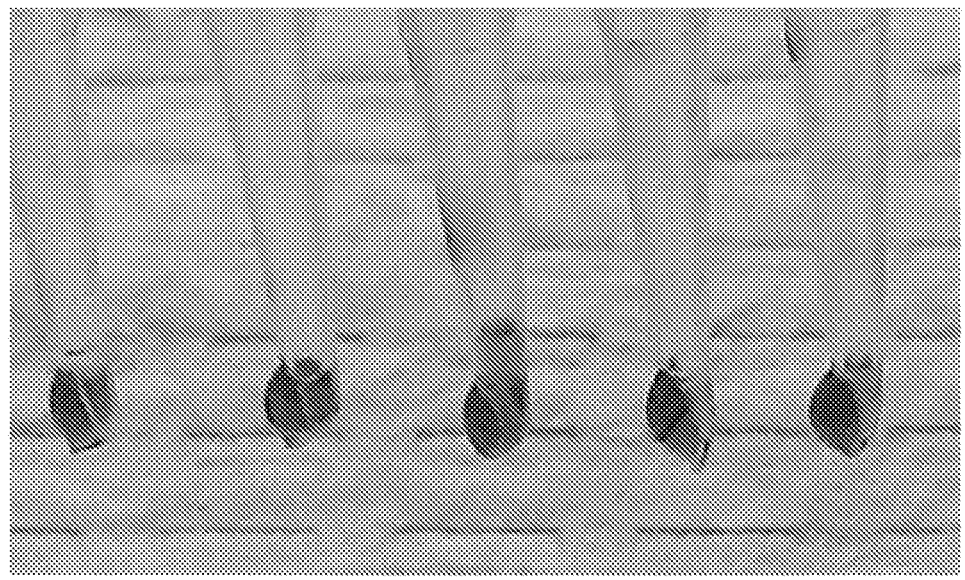
FIG. 3 shows the BioActivators prepared by aspirating 5 µl of low melt agarose containing primary human hepatocytes and dispensing 4 µl to form a droplet on the end of a pipette tip. In this iteration, a single prong holds the gelled agarose cell bead on the end of the tip.

FIG. 3 shows an image of a BioActivator (300) system in accordance with some embodiments of the present disclosure. The substance to be secured can be formed as a droplet on the end of the tip and can be secured by the securing structure (103). FIG. 3 shows, for example, that the BioActivators can be loaded with a droplet of sample on the end of a pipette tip (101), which is held in place by the securing structure (103). The chemical or biological sample (droplet) can be any substance which is capable of being held by the securing structure (103), such as a cell, or subcellular fractions (microsomes, mitochondria, or intact nucleus, for example). The sample can also be any cellular component, such as proteins, mRNA, DNA, diffusible agents, such as cytokines, hormones, drugs, or fatty acids. The sample can also be a chemical sample. The cell, for example, can be cultured in a gel-like substance that can be secured by the securing structure (103). Examples of the type of sample than can be secured by the securing structure (103) includes, but is not limited to, methylcellulose, agarose, agar or plasma clot. In one example, cells can be grown in the sample. The substance can be solidifiable, or can remain in a gel-like state. In one example, the substance can be a gelled agarose cell bead. In some embodiments, the substance can be a gel substance containing cells, and the gel can be cured while secured on the pipette tip by, for example, exposing the gel to lower temperature, light, ultraviolet (UV) radiation, and/or pH neutralization.

The modified pipette tips disclosed herein can be utilized in conjunction with a variety of dispensing devices, including manual dispensers (e.g., pipettors) and automated dispensers. A dispenser is a device that, when attached to the upper end of a pipette tip (the larger opening end), applies negative pressure to acquire fluids, and applies positive pressure to dispense fluids. The lower or distal portion of a dispenser (typically referred to as the barrel or nozzle) is placed in contact with the upper end of the pipette tip and held in place by pressing the barrel or nozzle of the dispenser into the upper end of the pipette tip. The combination then can be used to manipulate liquid samples.

A row of pipettes (100) can be inserted into a microtiter plate (200) for testing. The pipettes disclosed herein can be part of an automated system. A variety of automated pipettes are known to those of skill in the art. Automatic pipette machines or robots are used in the chemical and biological fields to automatically pipette fluids from one place to another, without the need for direct human involvement. Generally, automated pipette robots have three axes of motion to allow a moveable tip head to access different containers with fluid samples in a given area. One class of robots are known as θ-z-θ robots which combine rotational (θ) and vertical (z) motion of a robot arm holding the tip head with rotational (θ) motion of a carousel that holds the samples, thereby allowing the tip head to access the samples on the carousel. A more common class of robots are x-y-z gantry style robots (e.g. BioMek FX™, Qiagen™ Biorobots™, Agilent Bravo™) where the moveable tip head moves along one vertical axis and two orthogonal horizontal axes of motion. To avoid contamination, many automatic pipette machines use disposable pipette tips. Typically, the tip head on these robots has one or more nozzles that receive a pipette tip.

Also disclosed is an array of BioActivators (300) ready to insert into a plate (200) for testing. Any type of plate can be used that is compatible with the BioActivator system. For example, the plate can be a microtiter (also referred to as a microplate, microwell plate, or multiwall), which is a flat plate with multiple "wells" used as small test tubes. A microplate typically has 6, 12, 24, 48, 96, 384 or 1536 sample wells arranged in a 2:3 rectangular matrix. The microplate can also have 3456 or 9600 wells, and an "array tape" product has been developed that provides a continuous strip of microplates embossed on a flexible plastic tape, for example.

The BioActivator (300) disclosed herein can be a non-static test systems such as a microfluidic test system. These systems can be single, multiple or linked chambers of which media flows through. The BioActivator can be inserted anywhere in the microfluidic stream.

The BioActivator (300) can also be used with any system having multiple wells. For example, a 4000 well "microbubble" platform, which is useful with rare, difficult to get cell types (i.e., hair cells from inner ear, secretory cells from the salivary gland). Any type of multiple well plate can be used with the present invention. Such devices are known to those of skill in the art.

Figure 4:
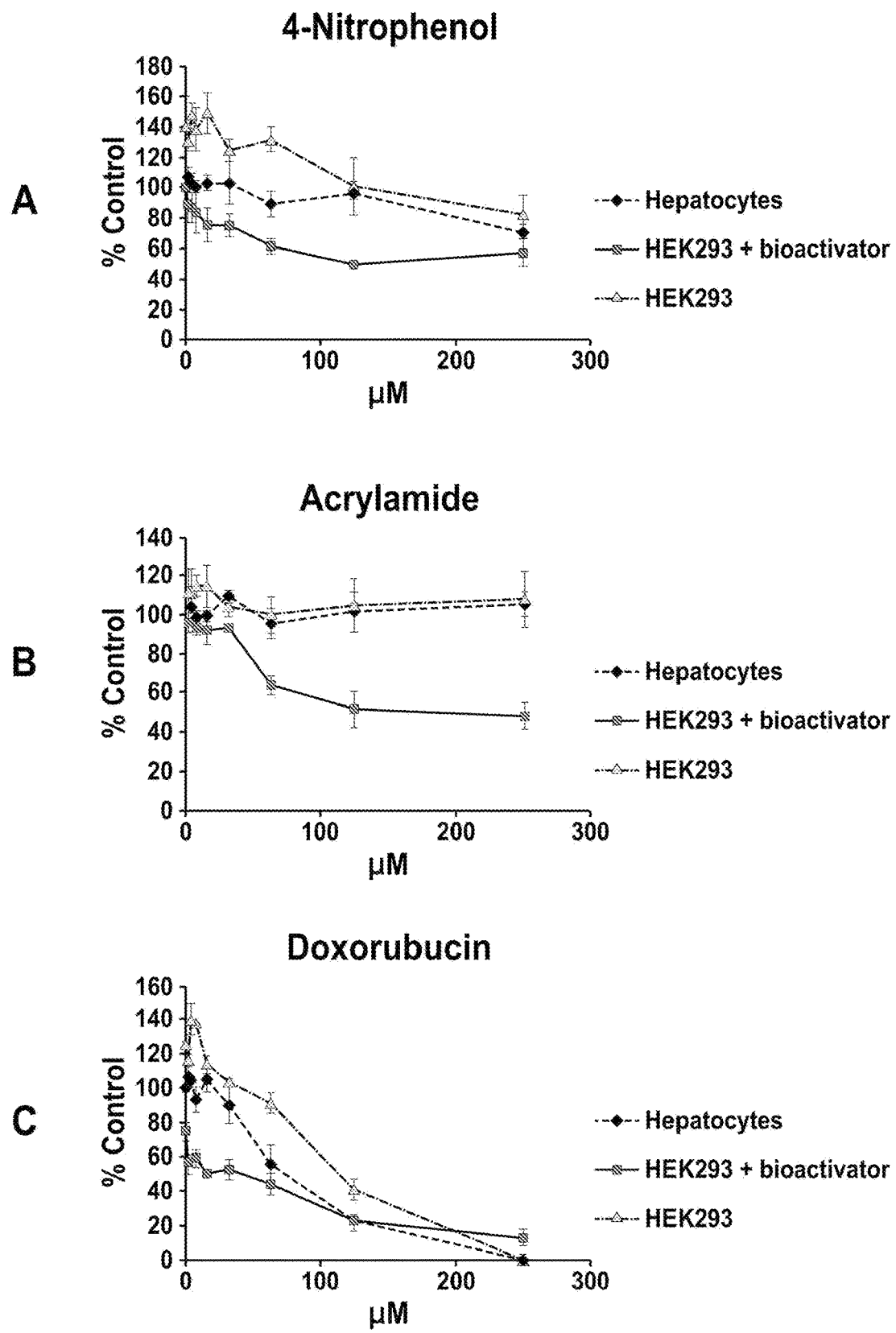
FIGS. 4A-I show the concentration responses for 9 chemicals (4-nitrophenol, acrylamide, doxorubicin, 6-aminochrysene, 8-methoxypsorlen, benzo[a]pyrene, cyclophosphamide, 2-napthylamine, and aflatoxin B1) treated 24 for hours to HEK293±bioactivation. In these experiments, BioActivators and hepatocyte free agarose beads were co-cultured in 384 microtiter plates with HEK293 cells. Following 24 hour incubation, the effect of the chemicals on HEK293 viability was assessed by removing the BioActivators from the HEK293 cell plate, and decanting the treatment media and adding CellTiter Glo® viability indicator. In addition, the effect of the treatment chemicals on hepatocyte viability was assessed by inserting the BioActivators from the HEK293 cell plate into a 384 well plate containing CellTiter Glo® viability indicator. All values are mean±SD (N=3).
Figure 4:
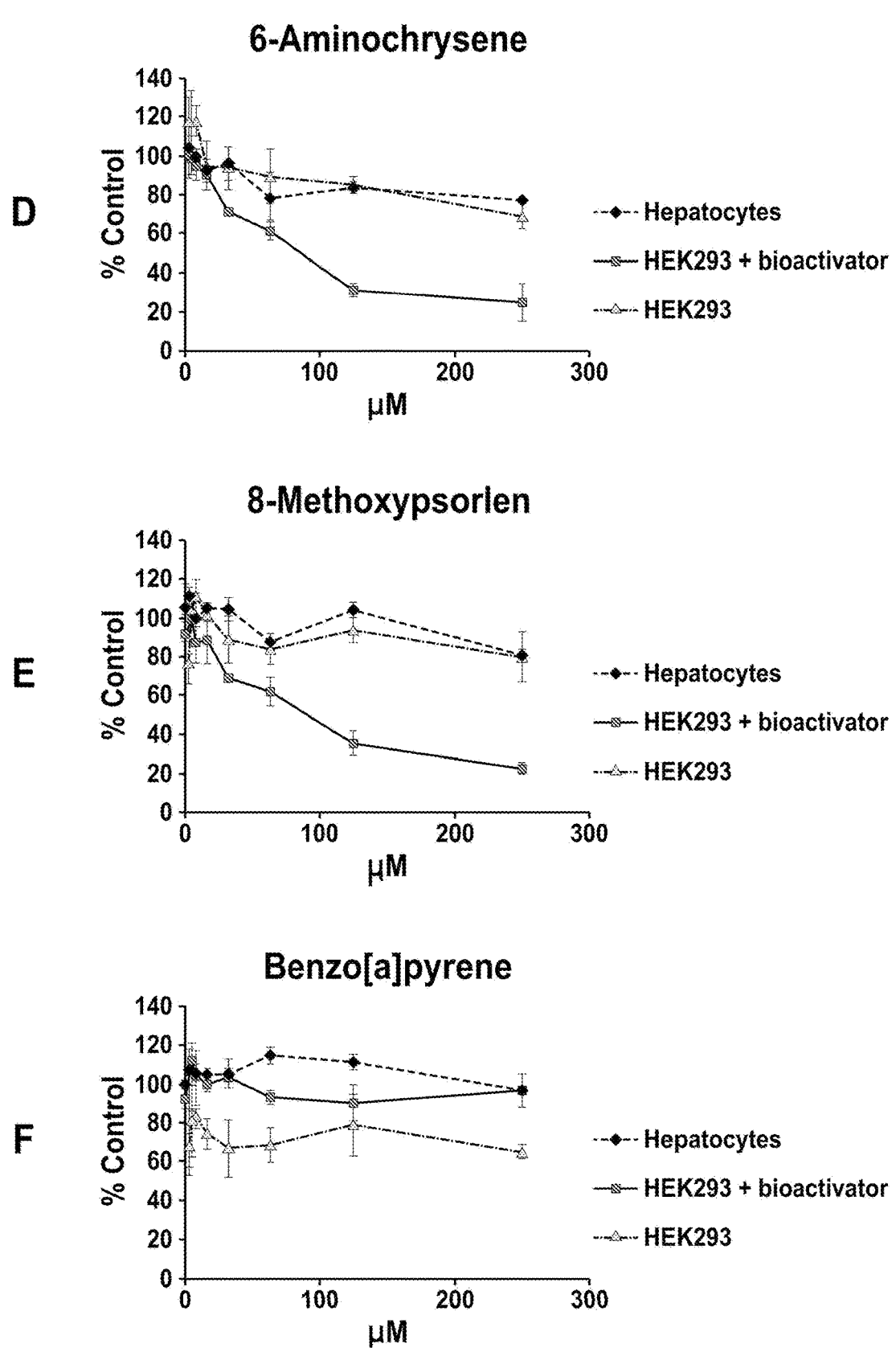
Figure 4:
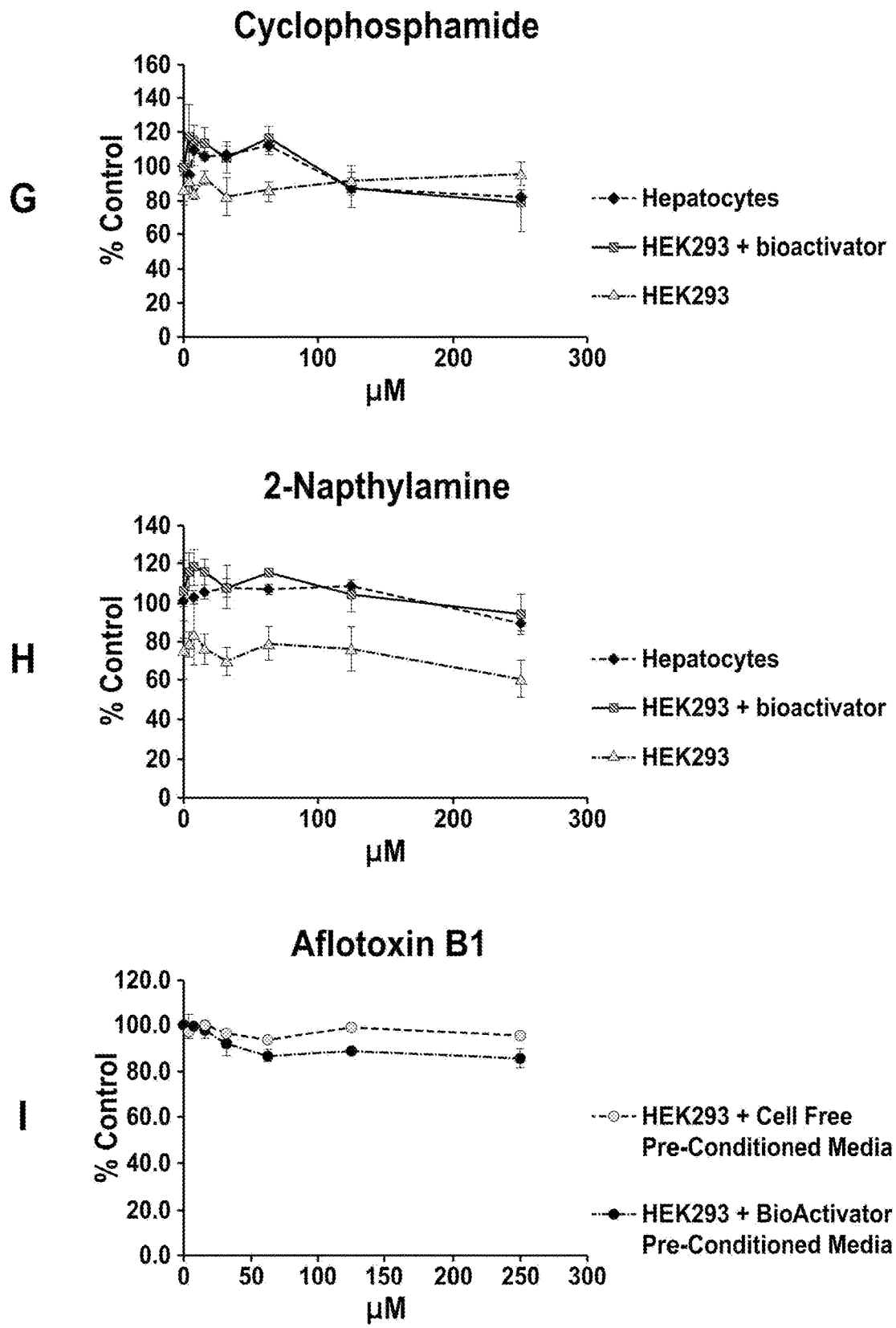
Figure 5:
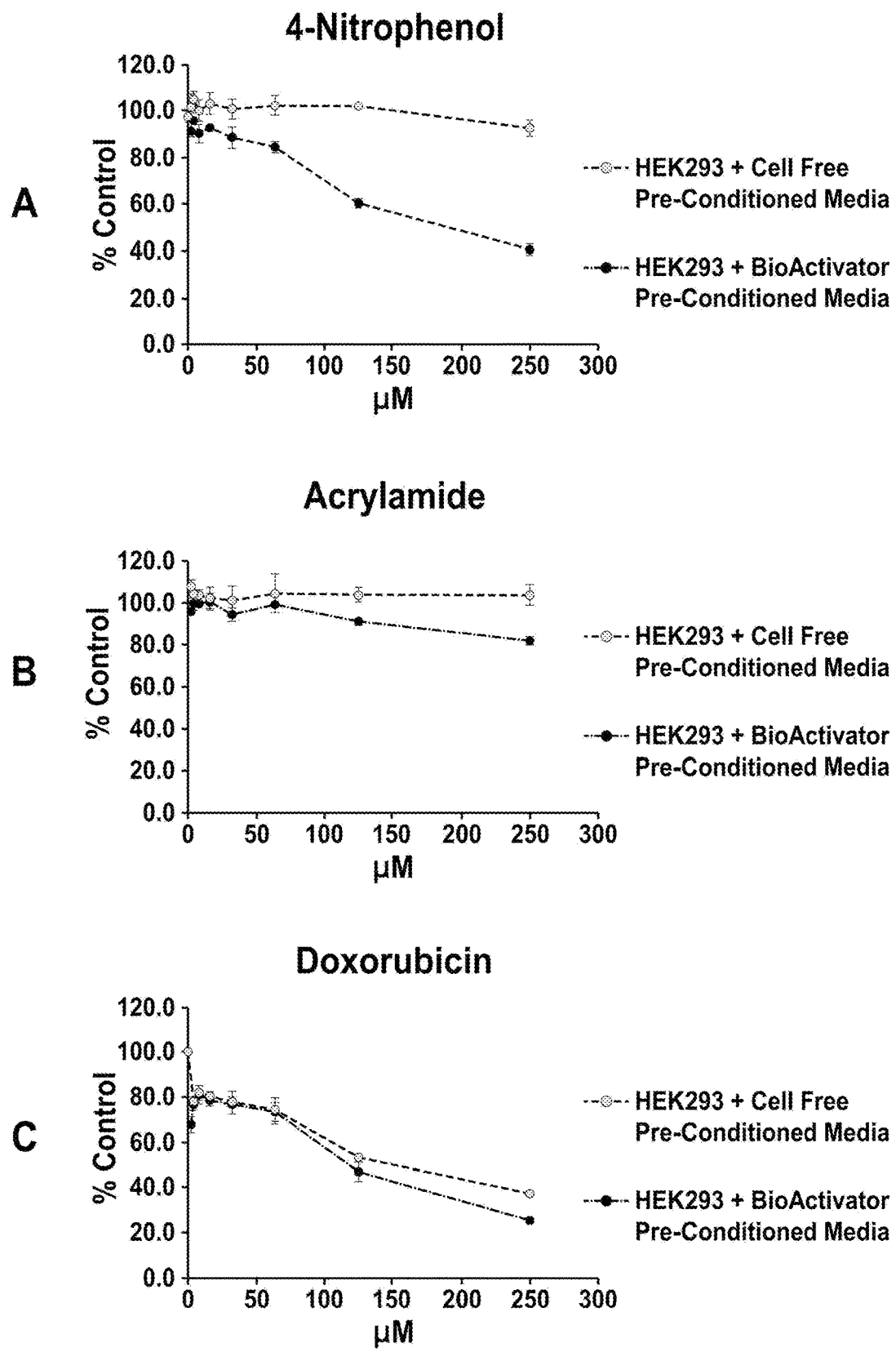
FIGS. 5A-I shows the concentration responses for 9 chemicals (4-nitrophenol, acrylamide, doxorubicin, 6-aminochrysene, 8-methoxypsorlen, benzo[a]pyrene, cyclophosphamide, 2-napthylamine, and aflatoxin B1) pre-treated 24 hours to BioActivators or cell free agarose beads. Following the pre-conditioning step the drug media was transferred in 384 microtiter plates containing HEK293 cells for an additional 24 hours. The effect of the pre-conditioned chemicals on HEK293 viability was assessed by decanting the treatment media and adding CellTiter Glo® viability indicator. All values are mean±SD (N=3).
Figure 5:
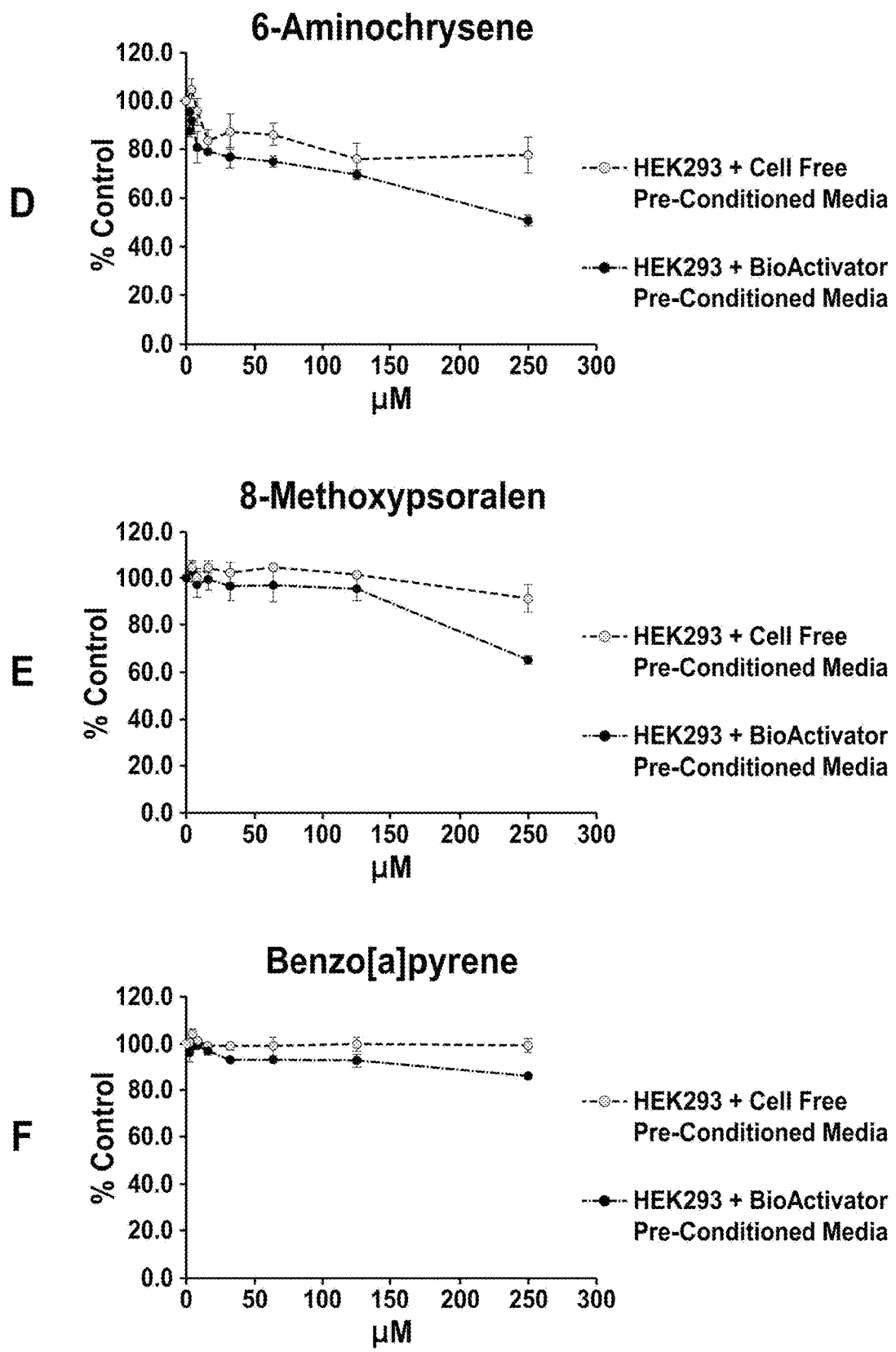
Figure 5:
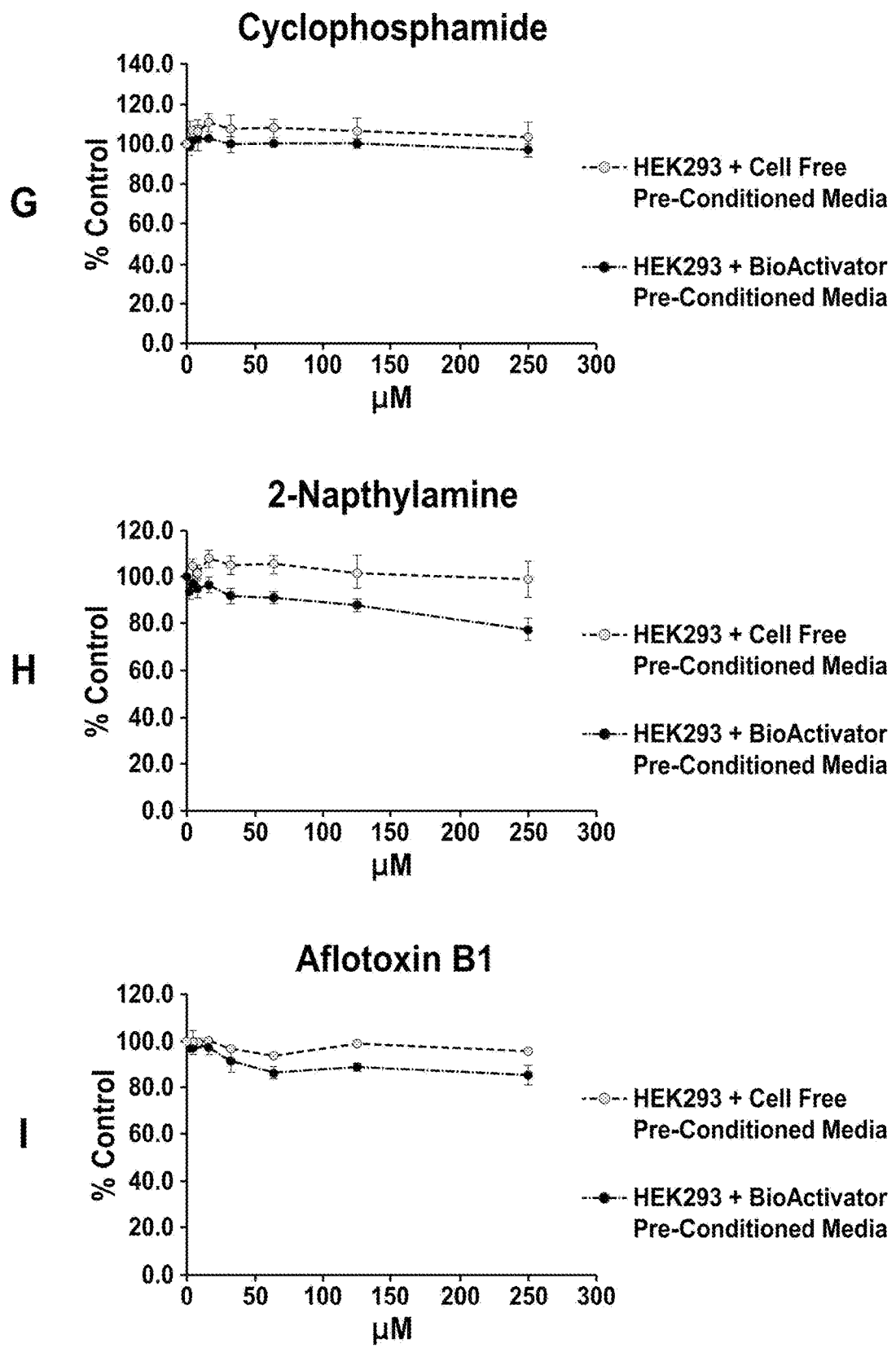

Each well of a microplate typically holds somewhere between tens of nanoliters to several milliliters of liquid. Wells can be either circular or square. For compound storage applications, square wells with close fitting silicone capmats are preferred. Microplates can be stored at low temperatures for long periods (such as cryopreserved), and may be heated to increase the rate of solvent evaporation from their wells and can even be heat-sealed with foil or clear film. In one example, an extended skirt can be used to adjust for the BioActivator to insert to the proper depth in the test plate. The wells can be filled with any test reagent, or can be filled with a storage medium to preserve cells in the sample encapsulated by the securing structure (103). Examples of test reagents that can be used in the wells can be seen in FIGS. 4, 5, and 9, discussed in further detail below.

Figure 6:
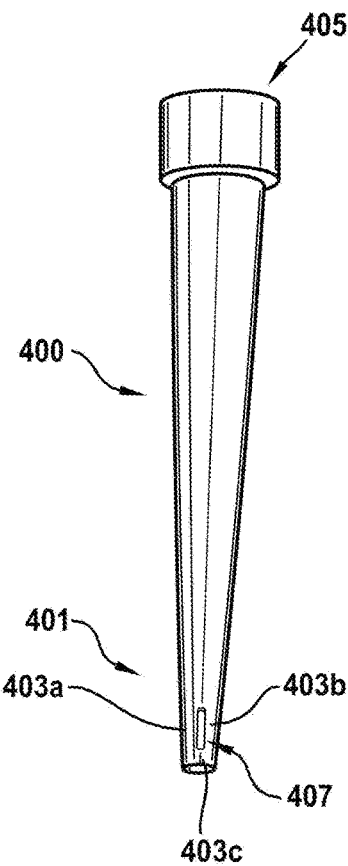
FIG. 6 shows modified pipettes with an opening for receiving and/or securing a sample, according to one embodiment of the present disclosure.
Figure 7:
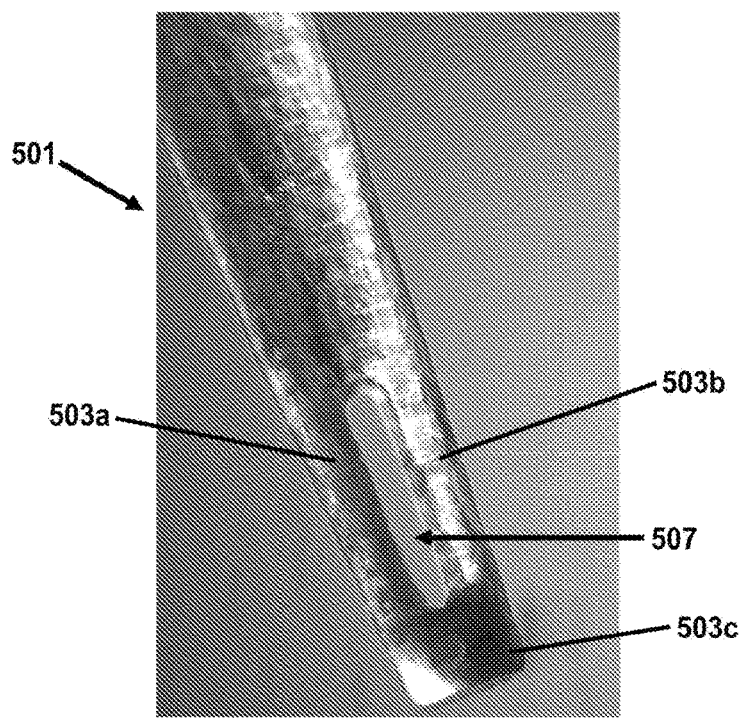
FIG. 7 shows a photomicrograph at 12.5× of a distal end portion tip of a pipette with a defined opening for receiving and/or securing a sample, according to one embodiment of the present disclosure.

Referring to FIGS. 6-8, 10, and 11, modified pipettes in accordance with various embodiments of the present disclosure include pipettes (e.g., 400) with one or more openings, such as a slot (407, 507, 607) in a securing structure (403, 503, 603) at a distal end portion (401, 501, 601) of the pipette. The features of FIGS. 6-8 are similar in some aspects to those embodiments shown for the "claw" and "prong" type securing structure (103) of FIGS. 1A, B, D, and FIG. 3, but in these latter embodiments, a defined opening (e.g., slot) is used to receive and/or hold the sample. In FIGS. 6-8, 10, and 11, like reference numerals are utilized to identify like components of the modified pipette (100) of FIGS. 1-3, with a prefixed "4", "5", or "6" utilized to identify the specific components of this embodiment in comparison to the claw securing structure (103) of previous embodiments. Certain functions and features of the embodiments of FIGS. 6-8, 10, and 11 of these embodiments are similar to those of the claw pipette tips (100) of the previous embodiments, and components that are different than those of the earlier-described embodiments are particularly emphasized below.

FIG. 6 shows a diagram of a pipette (400) according to one embodiment of the present disclosure which includes a slot (407) that is an opening of a securing structure (403) at a distal end portion (401) of the pipette 400 Side portions (403a, 403b) of the securing structure (403) extend in a substantially longitudinal direction (along the longitudinal axis of the distal end portion tip (401) of the pipette (400), opposite the proximal end 405), and a solid end portion (403c) is connected to the side portions (403a, 403b). By the configuration shown, a sample (e.g., liquid, chemical and/or biological substance) can access the pipette tip (401) and be secured therein by entering on either of two sides defined through the opening (407) from one side through to the other side in a direction perpendicular to the longitudinal axis (along the length from proximal end to distal end) of the pipette. The solid end portion (403c) prevents a substance from accessing the tip (401) at that location, such that the sample enters into the slot (407) instead. Although the opening (407) of the embodiment in FIG. 6 has a substantially rectangular-type shape with rounded inside corners and can be referred to as a part of a "slotted pipette tip", the "slot" (or, more generally, "opening"), as referred herein in accordance with various embodiments of the present disclosure may have other shapes, including, but not limited to a circular shape (see, e.g. opening shown in FIGS. 8A and 8B). It should be appreciated that the shape of the opening(s) in the embodiments of 6-8 (and FIGS. 10 and 11 as described further below) can be shortened, broadened, made more or less circular, or more or less square, for example, depending on a particular implementation desired, in order to optimize the access area of the liquid environment by diminishing as much of the solid pipette wall as practical.

The pipettes and/or pipette tips according to one or more of these embodiments shown in FIGS. 6-8, 10, and/or 11 can be made of any material known in the art to be compatible with cells, such as plastic material such as cyclic polyolefin, syndiotactic polystyrene, polypropylene, atactic polystyrene, PDMS, polyurethane, polycarbonate, or liquid crystal polymer or any other plastic material known to those skilled in the relevant art. The pipettes can be manufactured using injection molding or 3D printers, and can be made of silicone, or any other material useful with 3D printers. For example, the pipette and/or pipette tip shown in the embodiment of FIG. 6 can be constructed at least in part of polypropylene and may be formed by a 3D printing process. The pipette tip can also be coated with any material useful for preserving or enhancing the encapsulated sample. Examples include biological materials, such as proteins, collagen, or other material, or synthetic material used for promoting cell adherence. The surface can also be modified using an oxygen plasma discharge to make the surface more hydrophilic so that it becomes easier for cells to adhere to the surface.

FIG. 7 shows a photomicrograph at 12.5× of a distal end portion tip (501) of a pipette with an opening (507) for receiving and/or securing a sample, according to one embodiment of the present disclosure. Securing structure 503 is comprised of securing members that include member portions (503a, 503b, 503c) which partially define the opening (507).

Figure 8B:
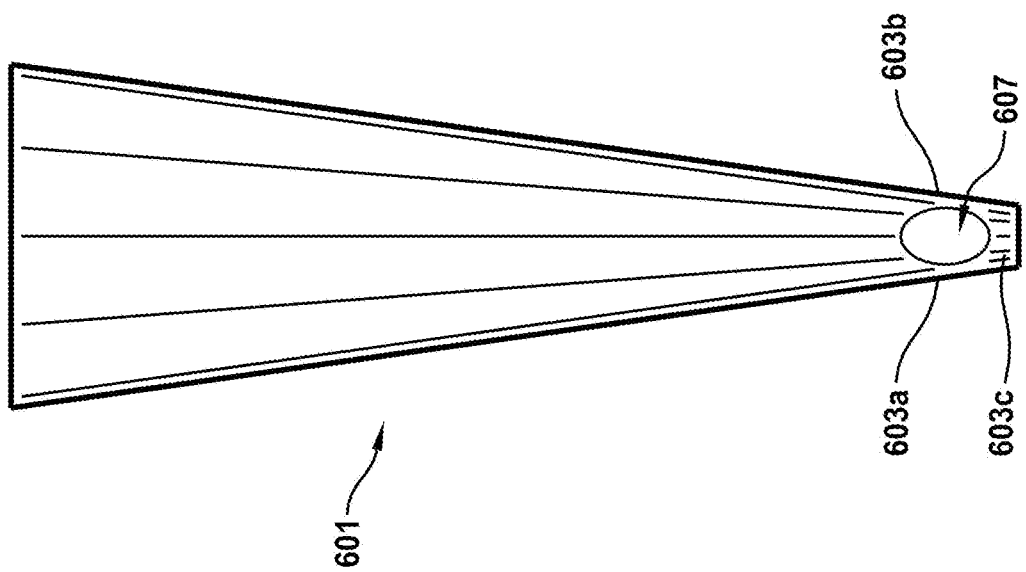
FIGS. 8A and 8B show a pipette tip with an opening defined in an end portion of the tip from one side through to the other, for receiving and/or securing a sample, according to one embodiment of the present disclosure.
Figure 8A:
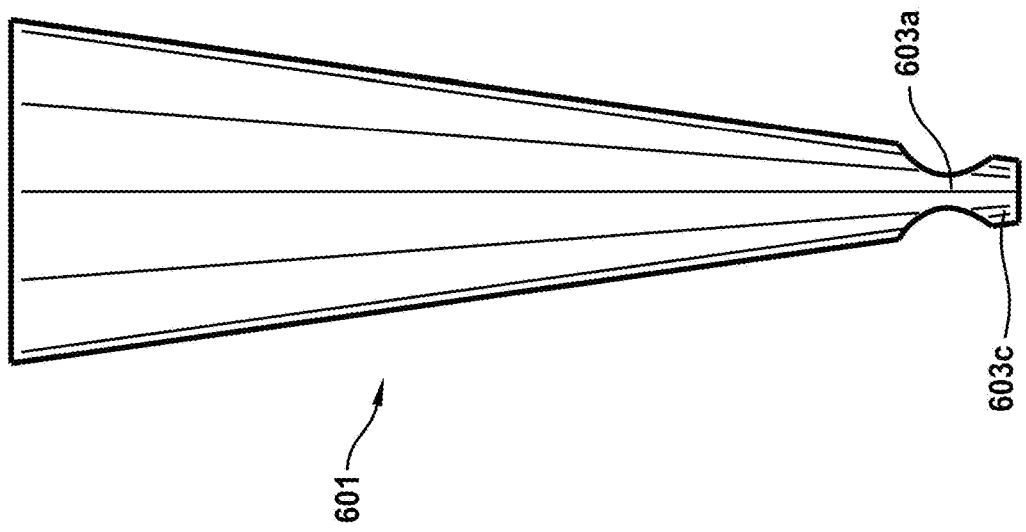

FIGS. 8A and 8B show a pipette tip (601) (distal end portion of pipette 600) (with an opening (607) defined in an end portion of the tip from one side through to the other, for receiving and/or securing a sample, according to one embodiment of the present disclosure. FIG. 8A shows one view of the pipette tip (601) and FIG. 8B shows a side profile view (the view of FIG. 8A rotated 90 degrees). As shown, the defined opening (607) is substantially circular on each side, and as shown in FIG. 8B, securing member portion (603a) of the securing structure (603) has concave-shaped sections, and when viewed at the side profile extends to an end tip portion (603c) to partially define the opening (607).

Figure 9:
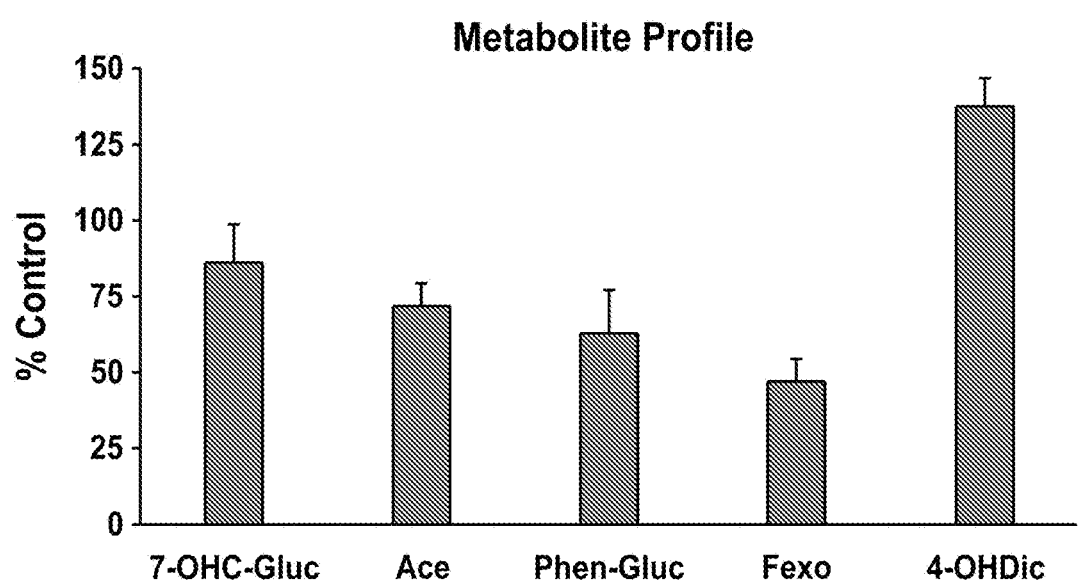
FIG. 9 shows a comparison chart of metabolites generated by the pipette tip according to the embodiment of FIG. 6 to the hepatocyte suspension cultures. Human primary hepatocytes metabolize coumarin to 7-hydroxycoumarin-glucuronide (7-OHC-Gluc), phenacetin to acetaminophen (Ace), phenolphthalein to phenolphthalein-glucuronide (Phen-Gluc), terfenadine to fexofenadine (Fexo) and diclofenac to 4-hydroxydicolfenac (4-OHDic) encapsulated within the slotted pipette tip compare favorably to control hepatocytes in short term suspension cultures, the gold standard for metabolism studies.

FIG. 9 shows a comparison chart of metabolites generated by the pipette tip according to the embodiment of FIG. 6 to the hepatocyte suspension cultures. Human primary hepatocytes metabolize coumarin to 7-hydroxycoumarin-glucuronide (7-OHC-Gluc), phenacetin to acetaminophen (Ace), phenolphthalein to phenolphthalein-glucuronide (Phen-Gluc), terfenadine to fexofenadine (Fexo) and diclofenac to 4-hydroxydicolfenac (4-OHDic) encapsulated within the slotted pipette tip compare favorably to control hepatocytes in short term suspension cultures, the gold standard for metabolism studies.

FIGS. 10A-10D show a pipette (700) with a pipette tip (701) configuration having an opening (707) defined at the tip (at the distal end portion of the pipette 700) from one side through to the other, for receiving and/or securing a sample, according to one embodiment of the present disclosure. FIG. 10A shows a front view illustrating the opening (707) and a securing structure (703). FIG. 10B shows a view taken from an end of the pipette (700), which illustrates the opening (707), securing member distal end section (703c), and part of the internal body portion (i.e., walls) of the pipette (700) that run from the proximal end (705) to the distal end (with tip 101). FIG. 10C is an enlarged view of the distal end tip (701) (see dashed and circled area A in FIG. 10A) with the securing structure 703 as shown in FIG. 10A. The securing structure is partially formed with securing member sections on the sides (703a, 703b) and distal end (703c). FIG. 10D is a side perspective view of the pipette (700) shown in FIGS. 10A-10C. The pipette (700) of the embodiment of FIGS. 10A-10D may be formed by a molding process in which the mold closing direction creates the slot (opening) 707.

FIGS. 11A-11C show a pipette (800) with a pipette tip (801) configuration having a plurality of openings (807a, 807b, 807c) defined at the tip (801) (i.e., at the distal end portion of the pipette, opposite the proximal end portion 805), according to one embodiment of the present disclosure. FIG. 11A shows a front view illustrating the pipette (800) with one of the openings (807) visible. FIG. 11B (which corresponds in part to the area encircled as A in FIG. 11A) shows a view taken from an end of the pipette (800), which illustrates the plurality of openings (807a, 807b, 807c) defined in a securing structure 803 (formed by tapering section 803a and end section 803b). The openings 807a, 807b, 807c) may be formed in a vertical direction from the distal end of the pipette (i.e., rather than forming them in a direction normal to the longitudinal axis of the pipette). FIG. 11C is a side perspective view of the pipette (800) shown in FIGS. 11A and 11B. The configuration of the openings (807a, 807b, 807c) may be shaped, sized, or spatially distributed alternatively to the specific embodiment of FIG. 11, for instance to manage desired or necessary volume uptake of a biological and/or chemical substance (e.g., drug). Furthermore, alternatively there may be more or less than three openings as needed according to particular implementations.

Although not described in detail here, the pipettes with tips as shown and described with reference to FIGS. 6-8, 10, and 11 may be used with microtiter plates (e.g., plate 200 described above) and/or BioActivator in similar ways to the use of the pipettes with tips that are shown in and described with respect to FIG. 1. For example, A row of pipettes (400) can be inserted into a microtiter plate (200) for testing. The pipettes disclosed herein can be part of an automated system. The slotted pipette tips (407, 507, 607) disclosed herein can be used with an array of BioActivators (300) ready to insert into a plate (200) for testing, as described in detail herein. Any type of plate can be used that is compatible with the BioActivator system.

The modified pipette tips disclosed herein can be any shape known in the art. For example, the pipette can be cone-shaped, or can be rectangular, tapering toward the end. In some embodiments, the pipette tips disclosed herein can have (i) an overall length of about 1.0 centimeters (cm) to about 8 cm; (ii) a fluid-emitting distal section terminus having an inner diameter of about 0.001 millimeters (mm) to about 0.5 mm and an outer diameter of about 0.02 to about 0.7 mm; and (iii) a dispenser-engaging proximal section terminus having an inner diameter of about ~1.5-8 mm. The pipette tips can be sized to fit commercial liquid handling robots, such as 96-well and 384-well configurations.

The wall of the proximal section of a pipette tip described herein sometimes is continuously tapered from the top portion, to a narrower terminus. The top portion generally is open and often is shaped to receive a pipette tip engagement portion of a dispensing device. The wall of a proximal section, in some embodiments, forms a stepped tapered surface. The angle of each taper in the proximal section is between about zero degrees to about thirty degrees from the central longitudinal vertical axis of the pipette tip, in certain embodiments. The wall thickness of a proximal section may be constant over the length of the section, or may vary with the length of the proximal section (e.g., the wall of the proximal section closer to the distal section of the pipette tip may be thicker or thinner than the wall closer to the top of the proximal section; the thickness may continuously thicken or thin over the length of the wall). A proximal section of a pipette tip may contain a filter, insert or other material.

The wall of the distal section of a pipette tip sometimes is continuously tapered from the wider portion, which is in effective connection with the proximal section, to a narrower terminus. The wall of the distal section, in some embodiments, forms a stepped tapered surface. The angle of each taper in a distal section is between about zero degrees to about thirty degrees from the central longitudinal vertical axis of the pipette tip, in certain embodiments. In some embodiments, the wall of the distal section forms stepped vertical sections. The wall thickness of a distal section may be constant along the length of the section, or may vary with the length of the section (e.g., the wall of the distal section closer to the proximal section of the pipette tip may be thicker or thinner than the wall closer to the distal section terminus; the thickness may continuously thicken or thin over the length of the wall). The distal section of a pipette tip generally terminates in an aperture through which fluid passes into or out of the distal portion. In some embodiments, the interior surface of the distal region is substantially smooth. In certain embodiments, the exterior surface of the distal region comprises a step. In some embodiments, a distal section of a pipette tip may contain a filter, insert or other material.

The BioActivator (300) disclosed herein can be cryopreserved. The advantage of encapsulation and cryopreservation of cells is to provide a simple and low cost method to produce an on-demand, single use competent bioactivation system. Furthermore, the system is flexible in that cells such as human hepatocytes can be encapsulated, cryopreserved and stored at one facility, then shipped to an external facility for thawing and use as needed. The BioActivator (300), when loaded with cells, can be prepared and used at any facility having robotic liquid handling capability and access to other cells of interest to assay testing. Another advantage of the BioActivator (300) is to maintain spatial separation between the co-cultured cells. This allows post treatment removal of the BioActivator (300) for unhindered processing of the assay plate.

Also disclosed herein is a method, comprising: securing a biological and/or chemical sample by a securing structure (103, 403) of a pipette (100), the securing structure comprising at least one mechanical securing member (104, 404) that is configured to mechanically secure the sample at the tip (101, 401) of the pipette, wherein the securing structure extends from the end of the tip and is in communication with, in one embodiment an opening (102) and in another embodiment a slot (407) defined at the tip for receiving and/or delivering a biological and/or chemical sample.

Therefore, disclosed herein is a method for securing the biological and/or chemical sample by the securing structure (103, 403) of the pipette (100) comprises aspirating a biological and/or chemical sample into the pipette and delivering a biological and/or chemical sample to the tip and into a position to be secured by the securing structure. This can be done in a very precise manner, so that the amount of sample aspirated into the opening (102) or slot (407) of the pipette (101, 401) can be quantified, and the subsequent amount of the sample eluted into the securing structure (103, 403) can likewise be precisely quantified. Precision measuring can be achieved through a variety of means known to those of skill in the art. For example, the low CV's associated with manual and robotic liquid handles can be used to deliver a set amount of cells in the delivery volume. Alternatively, statistical precision of an empirically measured biological function in an array of BioActivators can be used. For example, P450 Glo® reagent from ProMega® can be used to measure Cytochrome P450 3A4 activity across an array of BioActivators to show minimal variation.

The system disclosed herein can be used with any method in which pipetting is needed. For example, any modified pipettes disclosed herein can be used for a number of co-culture systems outside of drug metabolism, for example, testing drugs that cause two tissues to cross talk. For example, TNF-α can be used in a co-culture of hepatocytes and stellate cells. The TNF-α causes hepatocytes to release TGF-β which would then induce stellate cells to lay down a collagen scar, which can lead to cirrhosis, for example. The pipette tip can therefore be used in a large scale screening campaign to find a drug to halt this process.

The pipette tips described herein can be of any volume useful for dispensing fluids in combination with a dispensing device. Non-limiting examples of volumes useful for dispensing fluids in combination with a dispensing device, and described as non-limiting embodiments herein, include pipette tips configured in sizes that hold from 0 to 2 microliters, 0 to 10 microliters, 0 to 20 microliters, 1 to 100 microliters, 1 to 200 microliters, 1 to 300 microliters, and from 1 to 1250 microliters, for example. In some embodiments, the volumes pipette tips described herein can manipulate are larger than the volume designation given that particular pipette tip.

In one example, a gel can be used as the substance which is drawn into the pipette tip. Once a desired volume of gel has been aspirated, the pipette tip can undergo a "curation" process to harden the gel, which further fixes the gel in place on the pipette tip. For example, the gel can be exposed to a change in temperature, Calcium, pH, light, and/or ultraviolet (UV) radiation. The gel can also be exposed to various chemicals known in the art, which can increase the viscosity of the gel.

The BioActivator (300) can be adjusted so that the amount aspirated into the pipette (101, 401) is a particular volume, and that volume can correspond with the type of sample being secured. The sample eluted into the securing structure (103, 403) can then be either placed into well (201) of a plate (200) for testing, or cryopreserved and/or transported, as described herein. When the sample is placed into a well (201) for testing, the well can comprise a biological and/or chemical testing agent for interacting with the secured sample. The secured sample can be retained by the securing structure (103, 403) for at least a part of the testing. It can also be fully eluted into the well, if desired.

Also disclosed is a system for testing and/or transporting a biological and/or chemical sample, comprising: a plate (200) comprising a plurality of wells (201), a plurality of pipettes (300), each pipette (100, 400) being configured to be insertable into and removable from a respective well of the plurality of wells, wherein each of the pipettes comprises: a tip (101, 401) with, in one embodiment, a defined opening (102) or slot (407) for a biological and/or chemical sample, and a securing structure (103, 403) extending from the end of the tip (101, 401) and, in one embodiment, in communication with the opening (102) or slot (407), the securing structure having at least one mechanical securing member (104, 404) that is configured to secure the biological and/or chemical sample at the tip.

Various aspects of the disclosed technology may be still more fully understood from the following description of some example implementations and corresponding results. Some experimental data are presented herein for purposes of illustration and should not be construed as limiting the scope of the disclosed technology in any way or excluding any alternative or additional embodiments.

Example: Methods and Systems for Encapsulating and Cryopreserving Primary Human Hepatocytes on Pipette Tips Disclosed herein are methods and systems for encapsulating and cryopreserving primary human hepatocytes on the tips of custom 384-microtiter plate pipettes. Human hepatocytes are metabolically competent cell type which are often used to bioactivate test agents. Encapsulation is a cost effective and simple method to prepare the human hepatocytes for addition toxicology assays (referred to herein as ToxCast/Tox21 assays). Cryopreservation is an effective method to store large numbers of a bioactivation system to meet use at external test facilities.

The cryopreserved encapsulated hepatocytes (referred to herein as the "BioActivator") can be used in two ways. The first option is to pre-incubate the test compounds with a BioActivator and then sequentially transfer the media into a daughter plate for freezing and storage for later use, or, transfer the media immediately into the second assay for testing. This option allows the bioactivated media to be re-formatted to meet any 96-, 384- and 1536-well microtiter plate configuration. The second option is to co-culture the BioActivator into the media of any ongoing 96- or 384-well ToxCast/Tox21 assay. The two options provide the flexibility to store and ship large numbers of BioActivators to an external laboratory for on-demand thawing and use in ToxCast/Tox21 assays.

Human hepatocytes are one of the most metabolically competent cell type currently available. Encapsulation is a cost effective and simple method to prepare the human hepatocytes for addition to the ToxCast/Tox21 (toxicology) assays. Cryopreservation is an effective method to store large numbers of a bioactivation system to meet use at external test facilities. Two format options are can be used:

Option 1: pre-condition the test compounds in the BioActivator test system, sequentially transfer and freeze the conditioned media in daughter plates, or transfer the media immediately into the assay plate. This option allows the conditioned media to be formatted for testing in 96-, 384- and 1536-well microtiter plates.

Option 2: The BioActivator is thawed for co-culturing with the ongoing test assay.

The two formats provide an on-demand bioactivation system which can be stored and shipped for thawing and use at ToxCast/Tox21 (toxicology) external laboratories. These options are seen in FIGS. 2 and 3. The BioActivator was prepared and used in HEK293 cytotoxicity studies or for EROD and CypP450 Glo luminescence assays as 15,000 hepatocytes encapsulated on the tips of a custom prepared 384-well pipette. All studies involving collection of media for mass spectroscopy analysis were conducted with 50,000 hepatocytes encapsulated in the well of a 96 well microtiter plate.

Methods:

Agarose Encapsulation and Cryopreservation of Primary Human Hepatocytes for 384 Well Microtiter Plates.

Fresh human hepatocytes were received through the LTCDS (Liver Tissue Cell Distribution System) or purchased from Xenotech (Kansas, City, Kans.). A solution of 25% Percoll/DMEM was used to enrich for viable cells by centrifugation of the isolations at 50 g for 10 minutes. Supernate was aspirated and the hepatocyte cell pellet was resuspended in fresh DMEM/sodium pyruvate/HEPES for cell count and viability. The cells were pelleted and resuspended at $3\times10^6$ hepatocytes/ml in 1% low melt agarose/DMEM/sodium pyruvate/HEPES maintained at 38.5° C. The special pronged 384 well pipette tips were used to aspirate 5 μl of the low melt agarose followed by the dispensing of 4 μl to allow a droplet to form on the end of the pipette tip. The droplets were allowed to solidify at room temperature for 1 minute. The gelled BioActivator was then submerged into 50 μl cryopreservation media (DMEM/200 mM Trehalose/10% DMSO/20% FBS) dispensed into a 384 well polypropylene well (FIG. 2A). The BioActivator were incubated at RT in the media for 5 minutes after which the 384 well plate was placed on top of an aluminum block to allow uniform heat transfer and sealed inside an airtight container. The container was placed inside a second container filled with isopropanol to control cryopreservation rate at −80° C. Cell free agarose droplet tips were prepared and cryopreserved in an identical fashion.

The 384 well plate containing the cryopreserved cell or cell free BioActivators was rapidly thawed in a water bath at 37° C. The BioActivators and cell free agarose tips were transferred to a deep well reservoir containing 50 ml of pre-warmed DMEM complete media (DMEM supplemented with 10% FBS, 100 units penicillin and 100 μg streptomycin/ml) for 10 minutes to replace the cryopreservation media with media compatible with the test system.

Preparation of the DMSO Drug Stock and 2× Treatment Solution Plates.

A DMSO stock drug plate with a 8 point dose response compound concentrations was prepared from the 9 EPA compounds supplied as 50 mM DMSO stock by 2-fold dilutions in DMSO to achieve titers of 1:1, 1:2, 1:4, 1:8. 1:16, 1:32, 1:64 and 1:128. An intermediate 2× drug dosing plate was prepared just prior to use by diluting the stock drug plate compounds 1:100 in complete DMEM.

HEK293 384 Well Plate Preparation and Testing.

The day before drug exposure, HEK293 cells were harvested from cell culture flasks using standard trypsin treatment cell culture techniques. HEK292 were sub-cultivated into two 384 well plates at 5000 cells/25 μl/well from a suspension of 200,000 HEK293/ml in DMEM complete media. The cells were incubated at 37° C. in 5% $CO_2$ for 16-18 hours.

Once the BioActivator was ready for insertion into the HEK293 cell plate, 25 μl of a 2× solution of drug media was added to the HEK cells to achieve the final volume of 50 μl of 1× drug at 1:200, 1:400, 1:800, 1:1600, 1:3200, 1:6400, 1:12800 and 1:25600 titers equivalent to 250, 125, 62.5, 31.3, 15.6, 7.8, 3.9 and 2.0 μM (0.5% DMSO). The BioActivator was inserted into wells of the 1× drug treatment HEK293 cell plate for 24 hours at 37° C., 5% $CO_2$.

Cell Viability Assay.

The BioActivator unit was removed from the HEK293 cell plates and inserted into a clean 384 test plate containing 25 µl of fresh DMEM and 12.5 µl of CellTitre Glo® Luminescent Cell Viability Assay reagent (ProMega, Madison, Wis.). The media was decanted from the HEK293 drug test plate and replaced with 25 µl of fresh DMEM and 12.5 µl of CellTitre-Glo® Luminescent Cell Viability Assay reagent (ProMega, Madison, Wis.). After 20 minutes of incubation, cell viability was measured in the BioActivator and the HEK293 cell test plate by collecting luminescence for 0.5 seconds in a Spectramax M5 spectrophotometer.

Cyp 3A4 and Cyp1A2 Drug Metabolism Activity.

Hepatocytes were encapsulated in 1% agarose/DMEM at 2500 cells/W. The Cyp3A4 and Cyp1A2 activity was measured in 15000 hepatocytes over a 24 hour incubation period before or after cryopreservation. Cyp3A4 was assessed using ProMega CypP450 Glo® and Cyp1A2 activity using Ethoxy-Resorufin O-Demethlylase (EROD) assay. The Cyp3A4 assay was conducted according to the manufacture protocol and EROD according to the protocol described by Altman et al (Altmann B. et al. *Microstructuring of multiwell plates for three-dimensional cell culture applications by ultrasonic embossing*. Biomed Microdevices 2012; 14:291-301).

4-Probe Metabolite Testing.

Four compounds routinely for evaluating human hepatocyte metabolic competency are presented in Table 1. Probe metabolism was tested as a fresh hepatocyte suspension culture, as a fresh agarose gelled BioActivator and after thawing a cryopreserved BioActivator. In all three testing conditions 50,000 viable hepatocytes were tested as following: (a) as a suspension in 500 µl of probe media, or, (b) in 50 µl of gelled agarose submerged in 450 µl of probe media. Cryopreserved BioActivators were thawed for testing after 48 hours at -80° C. Probe media was collected from the 3 test conditions at 30 minutes and 18 hours. Ice-cold acetonitrile containing 10 µM chlorzoxazone (internal extraction standard) was added at a 2:1 ratio to the collected media. The extraction mixture was analyzed by LC MS/MS.

5 Probe Metabolite Testing.

Five metabolism probe compounds (Table 2) were tested in the BioActivator. BioActivators containing 50,000 hepatocytes and hepatocyte free beads were cryopreserved in 50 µl agarose in the wells of a 96 well microtiter plate. After thaw, 120 µl of 1× probe solution was added to the BioActivators and cell free agarose wells to initiate drug treatment. Duplicate test plates were set up to collect media and acetonitrile extracted cell/media at 30 minutes and at 18 hours.

Results: BioActivator Performance

Effect of Agarose Encapsulation and Cryopreservation on Primary Human Hepatocyte Viability.

A comparison between fresh isolated hepatocytes tested in suspension culture, solidified in agarose before cryopreservation and again after cryopreservation in two donor hepatocytes found that encapsulation reduced viability by 13-16% and cryopreservation by an additional 10-13% compared by CellTiter Glo® viability assay (Table 3). The 384 seeding density for human hepatocyte studies was increased by 25% to 15,000 hepatocytes per BioActivator to accommodate the viability loss due to encapsulation and cryopreservation.

Effect of Cryopreservation on EROD Activity.

A comparison between hepatocytes solidified in agarose before cryopreservation and again after cryopreservation in two donors found that cryopreservation reduced the Cyp1A2 conversion of 7-ethoxyresorufin to resorufin (EROD assay) by an average of 21% (Table 4).

Effect of Cryopreservation on Cyp3A4 Activity.

A comparison between hepatocytes solidified in agarose before cryopreservation and again after cryopreservation in two donors found that cryopreservation reduced the Cyp3A4 activity as measured by CYP450 Glo luminescence assay (ProMega, Madison, Wis.) by an average of 23% (Table 5).

Effect of Agarose Encapsulation and Cryopreservation on Primary Human Hepatocyte Compound Clearance and Metabolite Generation.

A cocktail of 10 uM Terfenadine, 10 uM Diclofenac, 10 uM Phenacetin and 10 uM Phenolphthalein was used to test the activity of Cyp3A4, Cyp2C9, Cyp1A2 and UDP-glucuronidation, respectively (Table 1). The comparison between fresh isolated hepatocytes from a single donor tested in suspension culture or solidified in agarose before cryopreservation and again after cryopreservation found that encapsulation and cryopreservation had minimal to a mild effect on the clearance of 4 probe test compounds at 30 minutes and 18 hours (Table 6). Phenacetin cleared at a slower rate in cryopreserved BioActivator but the remaining compounds were evidently minimally impacted. The metabolites of the probe compounds were evaluated in the 3 conditions at 30 minutes and 18 hours (Table 7). All metabolites were found in the 18 hour media incubated against BioActivators. The rate of generation of all metabolites were lower in the cryopreserved BioActivators compared to fresh suspensions but approximately the same or slightly lower when compared to the pre-cryopreservation BioActivator.

Cytotoxicity Testing 9 EPA Compounds in HEK293 Cells.

HEK293 cells were cultured in DMEM complete media using standard cell culture conditions. HEK293 cells were harvested by trypsin release from tissue culture flasks for sub-cultivation at 5000 cells/25 µl DMEM/well (200,000 cells/nil) into a Becton Dickinson Collagen Type 1 384 well microtiter plates and allowed to attach overnight at 37° C., 5% CO2. HEK293 cells were treated at 1X drug concentration at 0.5% DMSO by adding 25 µl of the 2× drug media to test plates. Thawed cryopreserved BioActivators and cell free agarose beads were inserted into the HEK293 plate for 24 hour incubation at 37° C., 5% CO2. Each drug concentration-response was tested in triplicate wells. At the termination of the treatment period the viability of the BioActivator system and the HEK293 test plate were tested by CellTiter Glo® viability reagent. The concentration response curves of this experiment are shown in FIG. 3 and the tabulated Lethal Concentration producing cell death in 50% of the cells (LC50) in Table 8. The BioActivator induced measurable LC50 responses for 4-Nitrophenol, Acrylamide, Doxorubicin, 6-Aminochrysene and 8-Methoxypsoralen. Doxorubicin produce a measurable LC50 in HEK293 incubated in a cell free agarose Finally, doxorubicin and aflatoxin B1 produced LC50 responses in BioActivators tested for hepatocyte viability post treatment as a co-culture with HEK293 cells. In a second experiment with different donor hepatocytes cryopreserved and thawed BioActivators and cell free agarose beads were used to pre-condition the 9 test compounds for 24 hours. The pre-conditioned media was sequentially transferred to 384 well plates containing 5000 HEK293 cells per well for an additional 24 hours of treatment. The concentration response curves of this experiment are shown (FIG. 4) and the tabulated Lethal Concentration producing cell death in 50% of the cells (LC50) in Table 9.

Results

Cryopreservation had minimal impact on the 24 hour hepatocyte clearance of diclofenac, terfenadine, phenolphthalein, and a mild impact on phenacetin clearance. Cryopreservation had little impact or very only slightly decreased the rate of metabolite generation of the probes compounds. The cytotoxicity of HEK293 cells treated to 9 test compounds co-incubated with the BioActivator found was increased for 4-Nitrophenol, Acrylamide, Doxorubicin, 6-Aminochrysene and 8-Methoxypsoralen compared to HEK293 cells treated to the 9 test compounds and a cell free agarose bead. No HEK293 cytotoxicity was found for Benzo [a]pyrene, cyclophosphamide, aflatoxin B1 or 2-Napthylamine up to the maximal tested concentration (250 µM) when co-cultured either with BioActivator or cell free agarose bead. However, cytotoxicity was evident in the Bioactivator hepatocytes treated to aflatoxin B1 and doxorubicin when tested for viability at the end of the co-culture period. Finally, 4-Nitrophenol, Doxorubicin and 6-Aminochrysene were found to produce cytotoxicity in HEK293 cells treated to test compounds pre-conditioned in the BioActivator as compared to test compounds pre-conditioned in cell free agarose beads.

TABLES

Table 1. Metabolism Probe Substrates List 1

| Substrate | Substrate 1X concentration | Incubation times | Marker Metabolite | Enzyme |
|---|---|---|---|---|
| terfenadine | 10 uM | 0.5/18 h | fexofenadine* | Cyp3A4 |
| phenacetin | 10 uM | 0.5/18 h | acetaminophen | Cyp1A2 |
| diclofenac | 10 uM | 0.5/18 h | 4-hydroxydiclofenac | Cyp2C9 |
| phenol-phthalein | 10 uM | 0.5/18 h | phenolphthalein-glucuronide | UGT |

*Fexofenadine metabolite is double hydroxylation from Cyp3A4 activity

TABLE 2

Metabolism Probe Substrates List 2

| Substrate | Substrate 1X concentration | Incubation times | Marker Metabolite | Enzyme |
|---|---|---|---|---|
| terfenadine | 100 uM | 0.5/18 h | hydroxyterfenadine | Cyp3A4 |
| phenacetin | 100 uM | 0.5/18 h | acetaminophen | Cyp1A2 |
| bupropion | 500 uM recommended, 250 um tested* | 0.5/18 h | 1-hydroxybupropion | Cyp2B6 |
| chlorzoxazone | 200 uM | 0.5/18 h | 6-hydroxy-chlorzoxazone | Cyp2E1 |
| 7-hydroxy-coumarin | 500 uM recommended, 250 uM tested* | 0.5/18 h | 7-hydroxy coumarin glucuronide | UGTs |

*received 50 mM stock samples which were prepared as 2X solutions at 500 uM in 1% solvent. The lower test concentration accommodates the maximum 0.5% solvent concentration.

TABLE 3

Comparison of CellTiter Glo ® Luminescence in Pre- and Post-Cryopreserved Human Hepatocytes Encapsulated in Agarose

| Trypan Blue Viability at Isolation | CellTiter Glo in fresh hepatocyte suspension at Isolation | Pre-Cryopreservation CellTiter Glo Lumines. | Post-Cryopreservation CellTiter Glo Lumines. | % Post/Pre (Mean ± SD) |
|---|---|---|---|---|
| Donor # 1 (Oct. 10, 2016): 37 year old female. Liver resection due to benign FNH ||||| 
| 8 square count | 20341.49677 | 16042.34933 | 14920.14369 | 93.0 |
| Viab. Non-Viab. | 18734.99089 | 17501.71241 | 14025.94242 | 80.1 |
| % Viable | 20156.77620 | 16350.69396 | 15103.21109 | 92.4 |
| 132 11 |  | 16499.01063 | 13989.47775 | 84.8 |
| 92% | Mean ± SD | Mean ± SD | Mean ± SD | (87.6 ± 6.2%) |
|  | 19743.7 ± 879.1 | 16631.6 ± 769.2 (84% of fresh suspension) | 16631.6 ± 769.2 (74% of fresh suspension) |  |
| Donor # 2 (Nov. 12, 2016): 49 year old male. Liver resection due to colon cancer metastasis |||||
| 8 square count | 14231.7826 | 12032.96756 | 9835.46731 | 81.7 |
| Viab. Non-Viab. | 12789.0098 | 11109.51643 | 9279.80311 | 83.5 |
| % Viable | 13423.8257 | 12332.08655 | 10015.45521 | 81.2 |
| 81 15 | Mean ± SD | 11937.89111 | 10147.1244 | 85.0 |
| 84% | 13481.5 ± 731.1 | 11998.43678 | 9526.77212 | 79.4 |
|  |  | 11403.03721 | 9061.93388 | 79.5 |
|  |  | Mean ± SD | Mean ± SD | (81.7 ± 2.7%) |
|  |  | 11802.3 ± 453.9 (87% of fresh suspension) | 9644.4 ± 427.32 (72% of fresh suspension) |  |

TABLE 4

EROD Activity in Pre- and Post-Cryopreserved BioActivators from 2 Donors

| Read # | Pre-cryopreservation EROD conversion (pmol/min/$10^6$ Hepatocytes) | Post-cryopreservation EROD conversion (pmol/min/$10^6$ Hepatocytes) | Percent Post-/Pre- EROD Activity (Mean ± SD) |
|---|---|---|---|
| Donor # 1 (Oct. 10, 2016): 37 year old female. Liver resection due to benign FNH ||||
| 1 | 2.63 | 2.16 | 82.9 ± 5.4% |
| 2 | 3.01 | 2.67 | |
| 3 | 2.58 | 2.01 | |
| Donor # 2 (Nov. 12, 2016): 49 year old male. Liver resection due to colon cancer metastasis ||||
| 1 | 1.23 | 1.03 | 75.2 ± 9.1% |
| 2 | 1.47 | 1.12 | |
| 3 | 1.51 | 0.99 | |

TABLE 5

Cyp3A4 Activity in Pre- and Post-Cryopreserved BioActivators from 3 Donors

| Read # | Pre-cryopreservation (RLU/min/$10^6$ hepatocytes) | Post-cryopreservation (RLU/min/$10^6$ hepatocytes) | Percent Post-/Pre- Cryopreservation Cyp3A4 Activity (Mean ± SD) |
|---|---|---|---|
| Donor # 1 (Oct. 10, 2016): 37 year old female. Liver resection due to benign FNH ||||
| 1 | 1074.367 | 965.126 | (88.4 ± 5.55) |
| 2 | 1158.164 | 954.177 | |
| 3 | 982.986 | 915.408 | |
| Donor # 2 (Nov. 12, 2016): 49 year old male. Liver resection due to colon cancer metastasis ||||
| 1 | 809.31 | 547.483 | (66.9 ± 0.7%) |
| 2 | 730.48 | 486.314 | |
| 3 | 681.95 | 452.453 | |
| Donor # 3 (Sep. 6, 2016) 58 year old female. Liver resection due to colon cancer metastasis ||||
| 1 | 810.123 | 685.980 | (83.1 ± 1.4%) |
| 2 | 822.920 | 676.701 | |
| 3 | 772.693 | 637.143 | |

TABLE 6

Percent of Parent Compound Remaining for 4 Probes Tested in Fresh Donor Hepatocyte Suspension or in Pre- and Post- Cryopreserved BioActivators[1]

| Test Condition | Phenolphthalein | | Terfenadine | | Phenacetin | | Diclofenac | |
|---|---|---|---|---|---|---|---|---|
| | 30 m | 18 h | 30 min | 18 hr | 30 min | 18 hr | 30 min | 18 hr |
| Hepatocyte Suspension | 56.6% | 6.0% | 29.0% | 13.3% | 47.4% | 14.6% | 74.6% | 18.1% |
| Pre-cryopreserved BioActivator | 63.8% | 7.6% | 55.7% | 12.9% | 77.0% | 23.0% | 67.8% | 20.2% |
| Post-cryopreserved BioActivator | 65.8% | 8.4% | 56.1% | 16.9% | 72.4% | 30.0% | 71.4% | 24.8% |
| Cell Free Suspension | 105.0% | 98.7% | 75.5% | 83.0% | 91.8% | 97.7% | 90.0% | 99.8% |
| Pre-cryopreserved cell free BioActivator | 99.7% | 101.8% | 74.3% | 72.9% | 101.4% | 101.1% | 87.1% | 88.1% |
| Post-cryopreserved cell free Bio Activator | 96.4% | 98.8% | 76.15 | 84.7% | 96.4% | 99.3% | 65.6% | 84.2% |

[1]Results presented as mean of duplicate wells.

TABLE 7

Metabolite Generation (pmol/min/10^6 hepatocytes) formed for 4 Probes Tested in Fresh Donor Hepatocyte Suspension or Pre- and Post- Cryopreserved BioActivators[1]

| Test Condition | Phenolphthalein ↓UGT[2] Ph.-glucuronide[3] | | Terfenadine ↓Cyp3A4[4] Fexofenadine | | Phenacetin ↓ Cyp1A2 Acetaminophen | | Diclofenac ↓ Cyp2C9 4-Hydroxydiclofenac | |
|---|---|---|---|---|---|---|---|---|
| | 30 m | 18 h | 30 min | 18 hr | 30 min | 18 hr | 30 min | 18 hr |
| Hepatocyte Suspension | 13.15 | 19.95 | 7.72 | 2.35 | 1.25 | 2.89 | 0.98 | 5.48 |
| Pre-cryopreserved BioActivator | 1.92 | 15.55 | 5.29 | 1.47 | 1.00 | 1.06 | NF | 3.67 |
| Post-cryopreserved BioActivator | 8.27 | 14.37 | 6.18 | 1.67 | 0.77 | 0.90 | NF | 3.05 |
| Cell Free Suspension | 0.12 | NF | 0.01 | 0.01 | NF | NF | NF | NF |
| Pre-cryopreserved cell free BioActivator | NF | 0.02 | 0.03 | NF | NF | NF | NF | NF |
| Post-cryopreserved cell free BioActivator | NF | NF | 0.03 | NF | NF | NF | NF | NF |

[1]Results presented as mean of duplicate wells.
[2]UGT—Uridine'5 Diphospho-Glucuronosyl Transferase.
[3]Phenolphthalein-glucuronide
[4]Generation of Fexofenadine from Terfenadine is a 2 step Cyp3A4 mediated hydroxylation

TABLE 8

HEK293 Cytotoxicity (LC$_{50}$ in μM) co-cultured 24 Hours with 9 EPA Test Compounds and BioActivators or Cell Free Agarose Beads

| Compound | HEK293 + BioActivator | HEK 293 + cell free agarose beads | BioActivator (Post Treatment) |
|---|---|---|---|
| 4- Nitrophenol | 101 ± 3.5[1] | >250 | >250 |
| Acrylamide | 167 ± 7.9 | >250 | >250 |
| Doxorubicin | 59 ± 5.1 | 108 ± 9.3 | 104 ± 4.6 |
| 6-Aminochrysene | 84 ± 2.0 | >250 | >250 |
| 8- Methoxypsorlen | 86 ± 6.1 | >250 | >250 |
| Benzo[a]pyrene | >250 | >250 | >250 |
| Cyclophosphamide | >250 | >250 | >250 |
| 2- Napthylamine | >250 | >250 | >250 |
| Aflatoxin B1 | >250 | >250 | 24 ± 3.0 |

[1]Results presented as Mean ± SD (N = 3).

TABLE 9

HEK293 Cytotoxicity (LC$_{50}$ in μM) Treated 24 h to BioActivator or Cell Free Agarose Bead Pre-Conditioned Media of 9 EPA Test Compounds

| Compound | HEK293 + BioActivator Pre-Conditioned Media | HEK 293 + Cell Free Agarose Bead Pre-Conditioned Media |
|---|---|---|
| 4- Nitrophenol | 199 ± 7.2[1] | >250 |
| Acrylamide | >250 | >250 |
| Doxorubicin | 71 ± 2.7 | 74 ± 3.3 |
| 6-Aminochrysene | 241 ± 9.8 | >250 |
| 8- Methoxypsorlen | >250 | >250 |
| Benzo[a]pyrene | >250 | >250 |
| Cyclophosphamide | >250 | >250 |
| 2- Napthylamine | >250 | >250 |
| Aflatoxin B1 | >250 | >250 |

[1]Results presented as Mean ± SD (N = 3)

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The scope of the present invention is indicated by the appended claims, rather than the foregoing description, and all changes that come within the meaning and range of equivalents thereof are intended to be embraced therein.

What is claimed is:

1. A pipette, comprising:
a tip with a defined first opening for a biological and/or chemical sample; and
a securing structure extending from the end of the tip and in communication with the defined first opening, the securing structure having at least one mechanical securing member that is configured to secure the biological and/or chemical sample at the tip; wherein the at least one mechanical securing member comprises securing member portions that at least partially define a second opening therebetween for receiving the biological and/or chemical sample; and further wherein the securing member portions comprise two side portions extending to a solid end tip portion.

2. The pipette of claim 1, wherein the at least one mechanical securing member comprises a single, prong member or claw-type member that is configured to mechanically secure the biological and/or chemical sample.

3. The pipette of claim 1, wherein the at least one mechanical securing member comprises a plurality of prong members and/or claw-type members oriented to substantially surround and hold the biological and/or chemical sample between the members.

4. The pipette of claim 1, wherein the securing structure comprises the second opening defined from one side of the pipette (through to an opposite side of the pipette, for receiving the biological and/or chemical sample at the one side of the pipette or the other side of the pipette.

5. The pipette of claim 4, wherein the second opening of the securing structure is substantially rectangular or circular in shape.

6. The pipette of claim 1, wherein the securing structure is configured to protect the secured sample from mechanical stress.

7. The pipette of claim 1, wherein the tip and securing structure are configured to permit the pipette to be insertable and removable into and out of a well of a plate (200) for testing and/or transporting the biological and/or chemical sample.

8. The pipette of claim 7, wherein the plate is a microtiter plate with a plurality of wells.

9. The pipette of claim 1, wherein the biological and/or chemical sample is formed as a droplet on the end of the tip and is secured by the securing structure.

10. The pipette of claim 1, wherein the biological and/or chemical sample comprises biological cells.

11. The pipette of claim 1, wherein the biological and/or chemical sample is comprised of biological cells encapsulated within a gel material.

12. The pipette of claim 11, wherein the biological cells encapsulated within a gel material are formed as a gelled agarose cell bead.

13. The pipette of claim 1, wherein the pipette is configured to aspirate a biological and/or chemical sample into the pipette and deliver a biological and/or chemical sample to the tip and into a position to be secured by the securing structure.

14. The pipette of claim 1, wherein the securing structure is configured to adhere the biological and/or chemical sample thereto.

15. The pipette of claim 1, wherein the at least one mechanical securing member is comprised of a biocompatible material.

16. A method, comprising:
securing a biological and/or chemical sample by a securing structure of a pipette, the securing structure comprising at least one mechanical securing member that is configured to mechanically secure the sample at the tip of the pipette, wherein the securing structure extends from the end of the tip and is in communication with defined first opening at the tip for receiving and/or delivering a biological and/or chemical sample; wherein the at least one mechanical securing member comprises securing member portions that at least partially define a second opening therebetween for receiving the biological and/or chemical sample; and further wherein the securing member portions comprise two side portions extending to a solid end tip portion.

17. The method of claim 16, wherein securing the biological and/or chemical sample by the securing structure of the pipette comprises aspirating a biological and/or chemical sample into the pipette and delivering a biological and/or chemical sample to the tip and into a position to be secured by the securing structure.

18. A system for testing and/or transporting a biological and/or chemical sample, comprising:
a plate comprising a plurality of wells;
a plurality of pipettes, each pipette being configured to be insertable into and removable from a respective well of the plurality of wells,
wherein each of the pipettes comprises:
a tip with a defined first opening for a biological and/or chemical sample, and
a securing structure extending from the end of the tip and in communication with the defined first opening, the securing structure having at least one mechanical securing member that is configured to secure the biological and/or chemical sample at the tips; wherein the at least one mechanical securing member comprises securing member portions that at least partially define a second opening therebetween for receiving the biological and/or chemical sample; and further wherein the securing member portions comprise two side portions extending to a solid end tip portion.

* * * * *

UNITED STATES PATENT AND TRADEMARK OFFICE
CERTIFICATE OF CORRECTION

PATENT NO. : 11,376,580 B2
APPLICATION NO. : 16/760187
DATED : July 5, 2022
INVENTOR(S) : Lawrence Vernetti et al.

It is certified that error appears in the above-identified patent and that said Letters Patent is hereby corrected as shown below:

In the Claims

In Column 25, Line 3 of Claim 4, the text "...pipette (through to an opposite side of the pipette, for..." should read --pipette through to an opposite side of the pipette, for--

In Column 25, Line 14 of Claim 7, the text "...well of a plate (200) for..." should read --well of a plate for--

In Column 26, Line 33 of Claim 18, the text "...sample at the tips;..." should read --sample at the tip;--

Signed and Sealed this
Eleventh Day of October, 2022

Katherine Kelly Vidal
*Director of the United States Patent and Trademark Office*